(12) United States Patent
Sorg et al.

(10) Patent No.: US 9,340,569 B2
(45) Date of Patent: May 17, 2016

(54) METHODS AND COMPOSITIONS FOR INHIBITING CLOSTRIDIUM DIFFICILE SPORE GERMINATION AND OUTGROWTH

(75) Inventors: Joseph Sorg, College Station, TX (US); Abraham L. Sonenshein, Brookline, MA (US)

(73) Assignee: Tufts University, Boston, MA (US)

( * ) Notice: Subject to any disclaimer, the term of this patent is extended or adjusted under 35 U.S.C. 154(b) by 430 days.

(21) Appl. No.: 13/126,687

(22) PCT Filed: Nov. 2, 2009

(86) PCT No.: PCT/US2009/005929
§ 371 (c)(1),
(2), (4) Date: Jul. 28, 2011

(87) PCT Pub. No.: WO2010/062369
PCT Pub. Date: Jun. 3, 2010

(65) Prior Publication Data
US 2011/0280847 A1    Nov. 17, 2011

Related U.S. Application Data

(60) Provisional application No. 61/110,747, filed on Nov. 3, 2008, provisional application No. 61/122,835, filed on Dec. 16, 2008, provisional application No. 61/150,136, filed on Feb. 5, 2009.

(51) Int. Cl.
*A61K 31/575* (2006.01)
*C07J 9/00* (2006.01)

(52) U.S. Cl.
CPC . *C07J 9/00* (2013.01); *A61K 31/575* (2013.01)

(58) Field of Classification Search
CPC .................................................... A61K 31/575
USPC ......................................................... 514/182
See application file for complete search history.

(56) References Cited

U.S. PATENT DOCUMENTS

| 4,793,948 | A | 12/1988 | Hatono et al. |
| 6,384,024 | B1 | 5/2002 | Gilat |
| 2004/0101525 | A1 | 5/2004 | Lin et al. |
| 2008/0254010 | A1 | 10/2008 | Sasser et al. |

FOREIGN PATENT DOCUMENTS

WO    WO9818474    *  5/1998

OTHER PUBLICATIONS

Murphy, G. M. et al., "Unsaturated Monohydroxy Bile Acids in Cholestatic Liver Disease", *Biochem J.*, 129(2):491-494 (The Biochemical Society, London, UK, Jan. 1, 1972).
Quistad, G. B. et al., "Xenobiotic conjugation: a novel role for bile acids", *Nature*, 296(5856):462-464 (USA, Apr. 1, 1982).
Extended European Search Report from corresponding application EP 09829458.0 dated Jun. 4, 2012.
Im, E. et al., "Novel bile acid derivatives induce apoptosis via a p53-independent pathway in human breast carcinoma cells", *Cancer Letters*, 163:83-93 (Elsevier, Ireland, 2001).
Ridlon, J. M. et al., "Bile salt biotransformations by human intestinal bacteria", *Journal of Lipid Research*, 47:241-259 (Usa, 2006).
Sorg, J. et al., "Bile Salts and Glycine as Cogerminants for Clostridium difficile Spores", *Journal of Bacteriology*, 190(7):2505-2512 (Usa, Apr. 2008).
International Search Report and Written Opinion from corresponding application PCT/US2009/005929 filed Nov. 2, 2009.

* cited by examiner

*Primary Examiner* — Barbara P Badio
(74) *Attorney, Agent, or Firm* — Alan W. Steele; Foley Hoag LLP

(57) ABSTRACT

Certain bile acids, including novel bile acids, and derivatives thereof can be used to inhibit the germination of *C. difficile* spores and/or the growth of *C. difficile* cells. The methods and compositions of the invention are useful for preventing and treating *C. difficile*-associated diseases, including but not limited to *C. difficile* colitis.

16 Claims, 7 Drawing Sheets

METHODS AND COMPOSITIONS FOR INHIBITING CLOSTRIDIUM DIFFICILE SPORE GERMINATION AND OUTGROWTH

FEDERALLY SPONSORED RESEARCH

This invention was made with government support under grant N01-AI30050 awarded by the National Institutes of Health. The government has certain rights in the invention.

BACKGROUND OF THE INVENTION

*Clostridium difficile* (*C. difficile*) is a gram-positive anaerobic *bacillus* and one of the most frequently recognized bacterial causes of diarrheal disease in hospitalized adults in industrialized countries. The microorganism can be acquired nosocomially and is present in environmental sources. Antibiotic-associated colitis and pseudomembranous colitis are frequently associated with cytotoxigenic *C. difficile*. The frequency of *C. difficile* toxin associated with antibiotic-associated colitis is 50-80% and with pseudomembranous colitis is 90-100%.

Despite available treatment for antibiotic-associated colitis and pseudomembranous colitis, relapses occur in 20-25% of patients. Vancomycin and metronidazole can be effective, but treated subjects are prone to relapse. Other treatment modalities include tolevemer, a toxin binding polymer (Louie et al. (2006) *Clin. Infect. Dis.* 43:411), and an antiparasitic medication, nitazoxanide (*Med. Letter Drugs Ther.* (2006) 48:89). Since relapses are so common, there is still a need for additional effective treatment and prevention of *C. difficile*-associated disease, particularly in humans.

SUMMARY OF THE INVENTION

The invention provides certain bile acids and salts thereof, methods of making same, methods of use thereof, and compositions thereof, useful for the treatment and prevention of *Clostridium difficile*-associated disease in a mammalian subject. Bile acids, salts thereof, and compositions of the invention can be used in the preparation of medicaments for the treatment of *Clostridium difficile*-associated disease, including but not limited to *C. difficile* colitis.

An aspect of the invention is a compound of Formula I

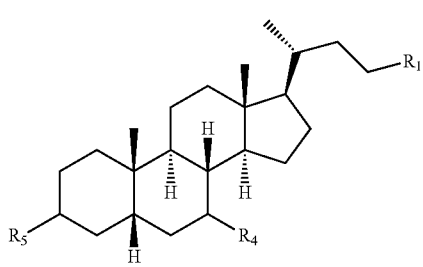

Formula I wherein $R_1$ is —CONHCH$_2$CH$_2$($R_3$); and each of $R_4$ and $R_5$ is independently selected from the group consisting of —H, —OH, —O($R_2$), and —OAcyl, wherein each $R_2$ is independently a straight or branched chain C1-C10 alkyl; and $R_3$ is selected from the group consisting of —CONH$_2$, —SO$_2$NH$_2$, and —CO$_2$($R_2$). In one embodiment this aspect further embraces pharmaceutically acceptable salts of these compounds.

Another aspect of the invention is a compound of Formula I

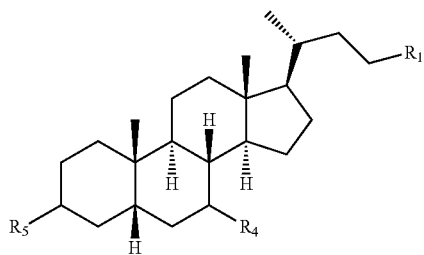

Formula I wherein $R_1$ is —CON($R_2$)CH$_2$CH$_2$($R_3$); and each of $R_4$ and $R_5$ is independently selected from the group consisting of —H, —OH, —O($R_2$), and —OAcyl, wherein each $R_2$ is independently a straight or branched chain C1-C10 alkyl; and $R_3$ is selected from the group consisting of —CONH$_2$ and —SO$_2$NH$_2$. In one embodiment this aspect further embraces pharmaceutically acceptable salts of these compounds.

An additional aspect of the invention is a compound of Formula I

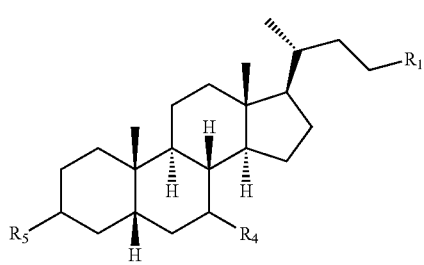

Formula I wherein $R_1$ is —CON($R_2$)CH$_2$CH$_2$($R_3$); and each of $R_4$ and $R_5$ is independently selected from the group consisting of —H, —OH, —O($R_2$), and —OAcyl, wherein each $R_2$ is independently a straight or branched chain C1-C10 alkyl; and $R_3$ is selected from the group consisting of —SO$_3$($R_2$) and —CO$_2$($R_2$), wherein when $R_4$ is either —H or —OH, $R_5$ is selected from the group consisting of —H, —O($R_2$), and —OAcyl; and when $R_4$ is either —O($R_2$) or —OAcyl, $R_5$ is selected from the group consisting of —H, —OH, —O($R_2$), and —OAcyl. In one embodiment this aspect further embraces pharmaceutically acceptable salts of these compounds.

An aspect of the invention is a probiotic composition comprising at least one strain of bacteria that is capable of metabolizing primary bile salts to secondary bile salts. In certain embodiments the at least one strain of bacteria is selected from *Clostridium scindens, Clostridium leptum*, and *Clostridium hiranonis* (also known as TO931).

In certain embodiments the probiotic is formulated for oral administration. In certain embodiments the probiotic is formulated for rectal administration.

An aspect of the invention is a method of preventing *Clostridium difficile*-associated disease in a mammalian subject, comprising administering to a mammalian subject at risk of developing *C. difficile*-associated disease an effective amount of a compound of Formula I

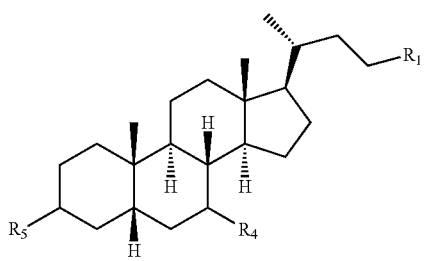

Formula I or a pharmaceutically acceptable salt thereof, wherein $R_1$ is selected from the group consisting of —$CO_2H$, —$CO_2(R_2)$, —$CONH_2$, —$CON(R_2)_2$, —$CONHCH_2CH_2(R_3)$, —$CON(R_2)CH_2CH_2(R_3)$, —$NH_2$, —$NH(R_2)$, and —$N(R_2)_2$; and each of $R_4$ and $R_5$ is independently selected from the group consisting of —H, —$NH_2$, —$NH(R_2)$, —$N(R_2)_2$, —OH, —$O(R_2)$, and —OAcyl, wherein each $R_2$ is independently a straight or branched chain C1-C10 alkyl; and $R_3$ is selected from the group consisting of —$CO_2H$, —$SO_3H$, —$CONH_2$, —$SO_2NH_2$, —$CO_2(R_2)$, and —$SO_3(R_2)$; to inhibit germination of *C. difficile* spores in the subject, thereby preventing *Clostridium difficile*-associated disease in the subject. In certain embodiments $R_1$ is selected from the group consisting of —$CO_2H$, —$CONH_2$, —$CON(R_2)_2$, —$CONHCH_2CH_2(R_3)$, and —$CON(R_2)CH_2CH_2(R_3)$; and each of $R_4$ and $R_5$ is independently selected from the group consisting of —H, —OH, —$O(R_2)$, and —OAcyl. In certain embodiments $R_4$ is —OH. In certain embodiments each of $R_4$ and $R_5$ is —OH.

In certain embodiments the compound of Formula I is chenodeoxycholate or a pharmaceutically acceptable salt thereof. In certain embodiments the compound of Formula I is ursodeoxycholate or a pharmaceutically acceptable salt thereof.

In certain embodiments $R_1$ is —$CONHCH_2CH_2(R_3)$; $R_3$ is —$CO_2H$ or —$SO_3H$; $R_4$ is —OH; and $R_5$ is —OH. In certain embodiments $R_1$ is —$CONHCH_2CH_2(R_3)$; $R_3$ is —$CO_2H$ or —$SO_3H$; $R_4$ is —H; and $R_5$ is —OH. In certain embodiments $R_1$ is —$CONHCH_2CH_2(R_3)$; and $R_3$ is selected from the group consisting of —$CONH_2$, —$SO_2NH_2$, and —$CO_2(R_2)$.

In certain embodiments $R_1$ is —$CON(R_2)CH_2CH_2(R_3)$; $R_2$ is methyl or ethyl; $R_3$ is —$CO_2H$ or —$SO_3H$; $R_4$ is —OH; and $R_5$ is —OH. In certain embodiments $R_1$ is —$CON(R_2)CH_2CH_2(R_3)$; $R_2$ is methyl or ethyl; $R_3$ is —$CO_2H$ or —$SO_3H$; $R_4$ is —H; and $R_5$ is —OH. In certain embodiments $R_1$ is —$CON(R_2)CH_2CH_2(R_3)$; and $R_3$ is selected from the group consisting of —$CONH_2$ and —$SO_2NH_2$.

In certain embodiments $R_1$ is —$CON(R_2)CH_2CH_2(R_3)$; $R_3$ is selected from the group consisting of —$SO_3(R_2)$ and —$CO_2(R_2)$; and each of $R_4$ and $R_5$ is independently selected from the group consisting of —H, —OH, —$O(R_2)$, and —OAcyl, wherein when $R_4$ is either —H or —OH, $R_5$ is selected from the group consisting of —H, —$O(R_2)$, and —OAcyl; and when $R_4$ is either —$O(R_2)$ or —OAcyl, $R_5$ is selected from the group consisting of —H, —OH, —$O(R_2)$, and —OAcyl.

In certain embodiments the *C. difficile*-associated disease is *C. difficile* colitis. In certain embodiments the *C. difficile*-associated disease is pseudomembranous colitis.

In certain embodiments the subject at risk of developing the *C. difficile*-associated disease is a subject that is receiving, is about to receive, or recently received an antibiotic associated with development of the *C. difficile*-associated disease. In certain embodiments the antibiotic associated with the development of the *C. difficile*-associated disease is selected from ampicillin, amoxicillin, clindamycin, fluoroquinolones, and cephalosporins.

In certain embodiments the subject is free of any other condition calling for administration of a compound of Formula I or a pharmaceutically acceptable salt thereof.

In certain embodiments the compound of Formula I or salt thereof is formulated for oral administration. For example, in one embodiment the administering involves orally administering. In certain embodiments the compound of Formula I or salt thereof is formulated for rectal administration. For example, in one embodiment the administering is rectally administering.

In one embodiment the subject is a human.

An aspect of the invention is a method of treating *Clostridium difficile*-associated disease in a mammalian subject. The method includes the step of administering to a mammalian subject having *C. difficile*-associated disease an effective amount of a compound of Formula I

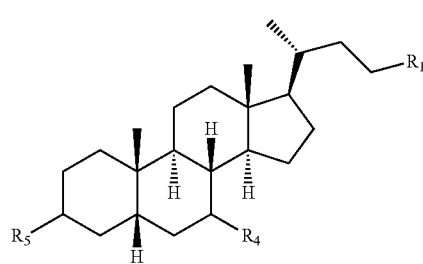

Formula I or a pharmaceutically acceptable salt thereof, wherein $R_1$ is selected from the group consisting of —$CO_2H$, —$OC_2(R_2)$, —$CONH_2$, —$CON(R_2)_2$, —$CONHCH_2CH_2(R_3)$, —$CON(R_2)CH_2CH_2(R_3)$, —$NH_2$, —$NH(R_2)$, and —$N(R_2)_2$; and each of $R_4$ and $R_5$ is independently selected from the group consisting of —H, —$NH_2$, —$NH(R_2)$; —$N(R_2)_2$, —OH, —$O(R_2)$, and —OAcyl, wherein each $R_2$ is independently a straight or branched chain C1-C10 alkyl; and $R_3$ is selected from the group consisting of —$CO_2H$, —$SO_3H$, —$CONH_2$, —$SO_2NH_2$, —$OC_2(R_2)$, and —$SO_3(R_2)$, to inhibit growth of *C. difficile* in the subject, thereby treating the *C. difficile*-associated disease. In certain embodiments $R_1$ is selected from the group consisting of —$CO_2H$, —$CONH_2$, —$CON(R_2)_2$, —$CONHCH_2CH_2(R_3)$, and —$CON(R_2)CH_2CH_2(R_3)$; and each of $R_4$ and $R_5$ is independently selected from the group consisting of —H, —OH, —$O(R_2)$, and —OAcyl. In certain embodiments $R_4$ is —OH. In certain embodiments each of $R_4$ and $R_5$ is —OH.

In certain embodiments the compound of Formula I is chenodeoxycholate or a pharmaceutically acceptable salt thereof. In certain embodiments the compound of Formula I is ursodeoxycholate or a pharmaceutically acceptable salt thereof.

In certain embodiments $R_1$ is —$CONHCH_2CH_2(R_3)$; $R_3$ is —$CO_2H$ or —$SO_3H$; $R_4$ is —OH; and $R_5$ is —OH. In certain embodiments $R_1$ is —$CONHCH_2CH_2(R_3)$; $R_3$ is —$CO_2H$ or —$SO_3H$; $R_4$ is —H; and $R_5$ is —OH. In certain embodiments $R_1$ is —$CONHCH_2CH_2(R_3)$; and $R_3$ is selected from the group consisting of —$CONH_2$, —$SO_2NH_2$, and —$OC_2(R_2)$.

In certain embodiments $R_1$ is —$CON(R_2)CH_2CH_2(R_3)$; $R_2$ is methyl or ethyl; $R_3$ is —$CO_2H$ or —$SO_3H$; $R_4$ is —OH; and $R_5$ is —OH. In certain embodiments $R_1$ is —$CON(R_2)CH_2CH_2(R_3)$; $R_2$ is methyl or ethyl; $R_3$ is —$CO_2H$ or —$SO_3H$; $R_4$ is —H; and $R_5$ is —OH. In certain embodiments $R_1$ is —CON($R_2$)$CH_2CH_2$($R_3$); and $R_3$ is selected from the group consisting of —CONH$_2$ and —SO$_2$NH$_2$.

In certain embodiments $R_1$ is —CON($R_2$)$CH_2CH_2$($R_3$); $R_3$ is selected from the group consisting of —SO$_3$($R_2$) and —OC$_2$($R_2$); and each of $R_4$ and $R_5$ is independently selected from the group consisting of —H, —OH, —O($R_2$), and —OAcyl, wherein when $R_4$ is either —H or —OH, $R_5$ is selected from the group consisting of —H, —O($R_2$), and —OAcyl; and when $R_4$ is either —O($R_2$) or —OAcyl, $R_5$ is selected from the group consisting of —H, —OH, —O($R_2$), and —OAcyl.

In certain embodiments the *C. difficile*-associated disease is *C. difficile* colitis. In certain embodiments the *C. difficile*-associated disease is pseudomembranous colitis.

In certain embodiments the subject having the *C. difficile*-associated disease is a subject that is receiving or recently received an antibiotic associated with development of the *C. difficile*-associated disease. In certain embodiments the antibiotic associated with the development of the *C. difficile*-associated disease is selected from ampicillin, amoxicillin, clindamycin, fluoroquinolones, and cephalosporins.

In certain embodiments the subject is free of any other condition calling for administration of a compound of Formula I or a pharmaceutically acceptable salt thereof.

In certain embodiments the compound of Formula I or salt thereof is formulated for oral administration. For example, in one embodiment the administering involves orally administering. In certain embodiments the compound of Formula I or salt thereof is formulated for rectal administration. For example, in one embodiment the administering is rectally administering.

In one embodiment the subject is a human.

An aspect of the invention is a method of reducing risk of developing *Clostridium difficile*-associated disease in a mammalian subject receiving antibiotic therapy. The method includes the step of comprising administering to a mammalian subject receiving antibiotic therapy and at risk of developing *C. difficile*-associated disease an effective amount of a compound of Formula I

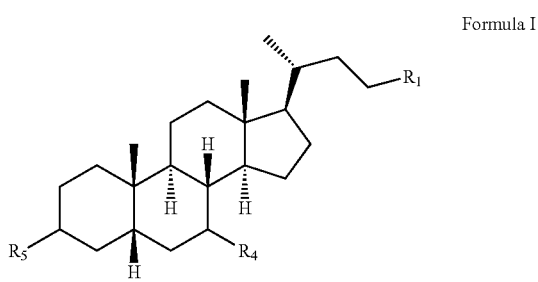

Formula I or a pharmaceutically acceptable salt thereof, wherein $R_1$ is selected from the group consisting of —CO$_2$H, —CO$_2$($R_2$), —CONH$_2$, —CON($R_2$)$_2$, —CONHCH$_2$CH$_2$($R_3$), —CON($R_2$)CH$_2$CH$_2$($R_3$), —NH$_2$, —NH($R_2$), and —N($R_2$)$_2$; and each of $R_4$ and $R_5$ is independently selected from the group consisting of —H, —NH$_2$, —NH($R_2$), —N($R_2$)$_2$, —OH, —O($R_2$), and —OAcyl, wherein each $R_2$ is independently a straight or branched chain C1-C10 alkyl; and $R_3$ is selected from the group consisting of —CO$_2$H, —SO$_3$H, —CONH$_2$, —SO$_2$NH$_2$, —OC$_2$($R_2$), and —SO$_3$($R_2$), to inhibit germination of *C. difficile* spores in the subject, thereby reducing the risk of developing *Clostridium difficile*-associated disease in the subject. In certain embodiments $R_1$ is selected from the group consisting of —CO$_2$H, —CONH$_2$, —CON($R_2$)$_2$, —CONHCH$_2$CH$_2$($R_3$), and —CON($R_2$)CH$_2$CH$_2$($R_3$); and each of $R_4$ and $R_5$ is independently selected from the group consisting of —H, —OH, —O($R_2$), and —OAcyl. In certain embodiments $R_4$ is —OH. In certain embodiments each of $R_4$ and $R_5$ is —OH.

In certain embodiments the compound of Formula I is chenodeoxycholate or a pharmaceutically acceptable salt thereof. In certain embodiments the compound of Formula I is ursodeoxycholate or a pharmaceutically acceptable salt thereof.

In certain embodiments $R_1$ is —CONHCH$_2$CH$_2$($R_3$); $R_3$ is —CO$_2$H or —SO$_3$H; $R_4$ is —OH; and $R_5$ is —OH. In certain embodiments $R_1$ is —CONHCH$_2$CH$_2$($R_3$); $R_3$ is —CO$_2$H or —SO$_3$H; $R_4$ is —H; and $R_5$ is —OH. In certain embodiments $R_1$ is —CONHCH$_2$CH$_2$($R_3$); and $R_3$ is selected from the group consisting of —CONH$_2$, —SO$_2$NH$_2$, and —CO$_2$($R_2$).

In certain embodiments $R_1$ is —CON($R_2$)CH$_2$CH$_2$($R_3$); $R_2$ is methyl or ethyl; $R_3$ is —CO$_2$H or —SO$_3$H; $R_4$ is —OH; and $R_5$ is —OH. In certain embodiments $R_1$ is —CON($R_2$)CH$_2$CH$_2$($R_3$); $R_2$ is methyl or ethyl; $R_3$ is —CO$_2$H or —SO$_3$H; $R_4$ is —H; and $R_5$ is —OH. In certain embodiments $R_1$ is —CON($R_2$)CH$_2$CH$_2$($R_3$); and $R_3$ is selected from the group consisting of —CONH$_2$ and —SO$_2$NH$_2$.

In certain embodiments $R_1$ is —CON($R_2$)CH$_2$CH$_2$($R_3$); $R_3$ is selected from the group consisting of —SO$_3$($R_2$) and —OC$_2$($R_2$); and each of $R_4$ and $R_5$ is independently selected from the group consisting of —H, —OH, —O($R_2$), and —OAcyl, wherein when $R_4$ is either —H or —OH, $R_5$ is selected from the group consisting of —H, —O($R_2$), and —OAcyl; and when $R_4$ is either —O($R_2$) or —OAcyl, $R_5$ is selected from the group consisting of —H, —OH, —O($R_2$), and —OAcyl.

In certain embodiments the *C. difficile*-associated disease is *C. difficile* colitis. In certain embodiments the *C. difficile*-associated disease is pseudomembranous colitis.

In certain embodiments the antibiotic is selected from ampicillin, amoxicillin, clindamycin, fluoroquinolones, and cephalosporins.

In certain embodiments the subject is free of any other condition calling for administration of a compound of Formula I or a pharmaceutically acceptable salt thereof.

In certain embodiments the compound of Formula I or salt thereof is formulated for oral administration. For example, in one embodiment the administering involves orally administering. In certain embodiments the compound of Formula I or salt thereof is formulated for rectal administration. For example, in one embodiment the administering is rectally administering.

In one embodiment the subject is a human.

An aspect of the invention is a method of inhibiting growth of *Clostridium difficile* in a mammalian subject. The method includes the step of administering to a mammalian subject in need thereof an effective amount of a probiotic comprising at least one strain of bacteria that is capable of metabolizing primary bile salts to secondary bile salts, to inhibit growth of *C. difficile* in the subject.

In certain embodiments the at least one strain of bacteria is selected from *Clostridium scindens, Clostridium leptum*, and *Clostridium hiranonis* (also known as TO931).

In certain embodiments the probiotic is formulated for oral administration. For example, in one embodiment the administering involves orally administering. In certain embodiments the probiotic is formulated for rectal administration. For example, in one embodiment the administering involves rectally administering.

In one embodiment the subject is a human.

An aspect of the invention is a method of preventing *Clostridium difficile*-associated disease in a mammalian subject. The method includes the step of administering to a mammalian subject at risk of developing *C. difficile*-associated disease an effective amount of a probiotic comprising at least one strain of bacteria that is capable of metabolizing primary bile salts to secondary bile salts, to inhibit growth of C. difficile in the subject, thereby preventing Clostridium difficile-associated disease in the subject.

In certain embodiments the C. difficile-associated disease is C. difficile colitis. In certain embodiments the C. difficile-associated disease is pseudomembranous colitis.

In certain embodiments the subject at risk of developing the C. difficile-associated disease is a subject that recently received an antibiotic associated with development of the C. difficile-associated disease. In certain embodiments the antibiotic associated with the development of the C. difficile-associated disease is selected from ampicillin, amoxicillin, clindamycin, fluoroquinolones, and cephalosporins.

In certain embodiments the at least one strain of bacteria is selected from Clostridium scindens, Clostridium leptum, and Clostridium hiranonis (also known as TO931).

In certain embodiments the probiotic is formulated for oral administration. For example, in one embodiment the administering involves orally administering. In certain embodiments the probiotic is formulated for rectal administration. For example, in one embodiment the administering involves rectally administering.

In one embodiment the subject is a human.

An aspect of the invention is a method of treating Clostridium difficile-associated disease in a mammalian subject. The method includes the step of administering to a mammalian subject having C. difficile-associated disease an effective amount of a probiotic comprising at least one strain of bacteria that is capable of metabolizing primary bile salts to secondary bile salts, to inhibit growth of C. difficile in the subject, thereby treating the C. difficile-associated disease.

In certain embodiments the C. difficile-associated disease is C. difficile colitis. In certain embodiments the C. difficile-associated disease is pseudomembranous colitis.

In certain embodiments the subject having the C. difficile-associated disease is a subject that recently received an antibiotic associated with development of the C. difficile-associated disease. In certain embodiments the antibiotic associated with the development of the C. difficile-associated disease is selected from ampicillin, amoxicillin, clindamycin, fluoroquinolones, and cephalosporins.

In certain embodiments the at least one strain of bacteria selected from Clostridium scindens, Clostridium leptum, and Clostridium hiranonis (also known as TO931).

In certain embodiments the probiotic is formulated for oral administration. For example, in one embodiment the administering involves orally administering. In certain embodiments the probiotic is formulated for rectal administration. For example, in one embodiment the administering involves rectally administering.

In one embodiment the subject is a human.

DETAILED DESCRIPTION OF THE INVENTION

Figure 1:
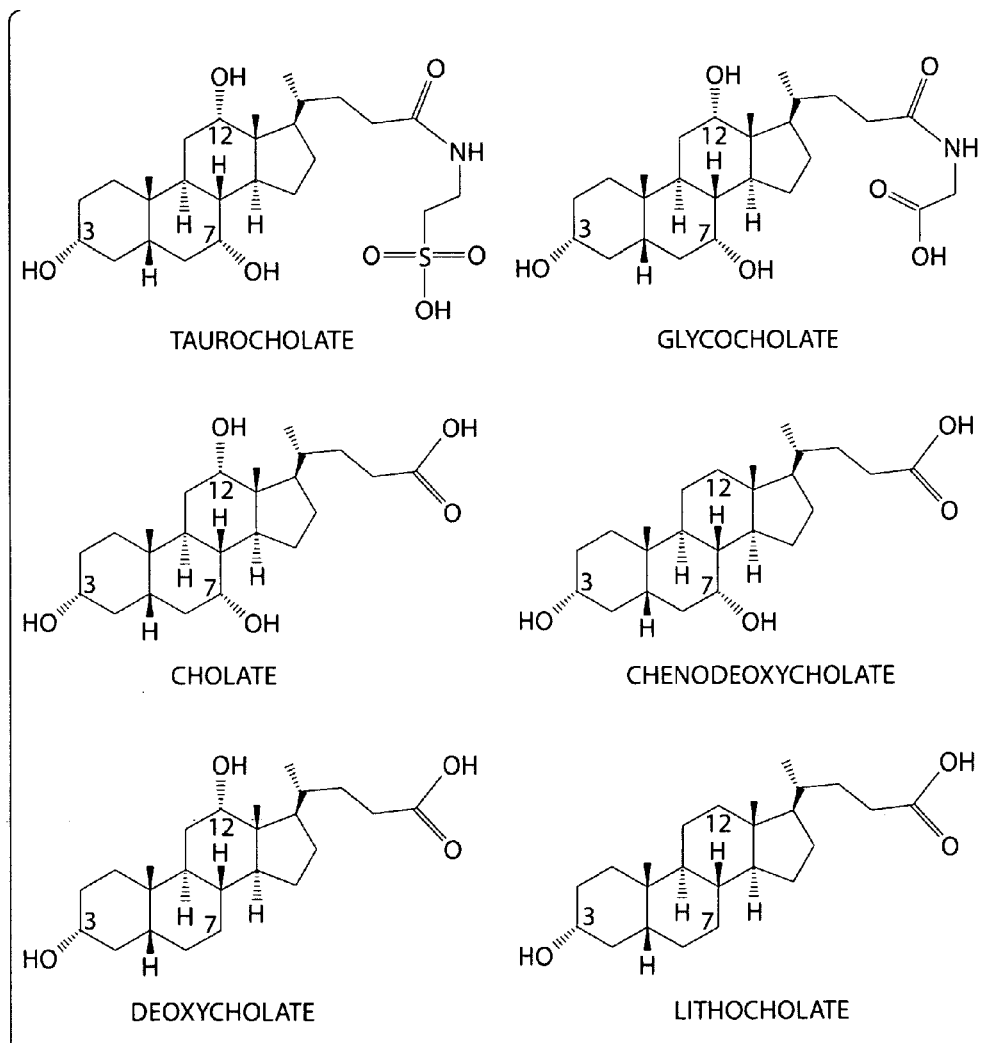
FIG. 1 depicts structural formulas of common primary and secondary bile acids. The primary bile salts cholate and chenodeoxycholate typically are conjugated with taurine or glycine (only taurocholate and glycocholate are shown). The normal intestinal microbial flora deconjugate the tauryl and glycyl group from cholate and chenodeoxycholate. The deconjugated primary bile salts are further metabolized by the microbial flora to deoxycholate and lithocholate, respectively.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The invention is based at least in part on the surprising discovery by the inventors that certain bile acids and their salts inhibit germination of *C. difficile* spores. Bile acids and salts thereof with this property have a 12-deoxy structure and include, for example, chenodeoxycholate and its 7β-hydroxy epimer ursodeoxycholate. Inhibiting germination of *C. difficile* spores results in inhibition of the downstream generation and growth of the vegetative state of *C. difficile* that can occur in the anaerobic environment of the large intestine. Accordingly, the invention concerns compositions and methods that are useful in the prevention and treatment of *C. difficile*-associated disease, including antibiotic-associated diarrhea (also known as *C. difficile* colitis) and pseudomembranous colitis.

Spore formation by *Clostridium difficile* is a significant obstacle to overcoming hospital-acquired *C. difficile*-associated disease. Spores are resistant to heat, radiation, chemicals, and antibiotics, making a contaminated environment difficult to clean. To cause disease, however, spores must germinate and grow out as vegetative cells.

Vegetative cells of *C. difficile* are exquisitely sensitive to oxygen. To survive outside the anaerobic environment of the large bowel, the bacterium has to be in the spore form. Thus, it is generally accepted that the spore form of *C. difficile*, acquired from the environment, initiates disease. Since toxins are produced by cells, not spores, the spores presumably germinate in the gastrointestinal tract, grow out as vegetative cells, and produce toxin. Any *C. difficile* bacteria that are excreted by the host, however, have to be in the spore form to survive for long periods. Although the morphological changes during sporulation are very similar in *Clostridium* and *Bacillus* species, sporulation and germination in *Clostridium* species are not as well studied as those in the model organism *Bacillus subtilis*. In brief, sporulation is initiated under conditions of nutrient limitation and leads to formation of an asymmetrically placed division septum that divides the cell into two unequal compartments, each of which contains one copy of the chromosome. The larger, mother cell compartment then engulfs the forespore and helps the forespore mature. Hilbert et al. (2004) *Microbiol. Mol. Biol. Rev.* 68:234-262. The addition of a peptidoglycan cortex and several layers of coat proteins precedes release into the environment by lysis of the mother cell. Henriques et al. (2007) *Annu. Rev. Microbiol.* 61:555-588.

Once released from the mother cell, the spore is metabolically dormant but highly resistant to many types of environmental insult. When conditions become suitable for growth, the spores germinate and grow out as vegetative cells. In *B. subtilis*, germination can be induced by L-alanine or by a mixture of asparagine, glucose, fructose, and potassium ions. Receptors involved in sensing these environmental cues are GerA, GerB, and GerK. Irie et al. (1996) *J. Gen. Appl. Microbiol.* 42:141-153; Moir et al. (1979) *J. Gen. Microbiol.* 124: 165-180. After the germinant is sensed, a large depot of calcium dipicolinate ($Ca^{2+}$-DPA) is released, the core hydrates, the cortex is degraded, and metabolism begins. Homologs of GerA, GerB, and GerK exist in several *Bacillus* species as well as in many *Clostridium* species but are absent in *C. difficile*, suggesting that *C. difficile* responds to different kinds of environmental cues. In fact, spore germination in different species is induced by a variety of germinants. For instance, for *Bacillus megaterium* spores, L-proline is a germinant, while purine ribonucleosides and amino acids act as cogerminants for *Bacillus anthracis* spores.

Germination and outgrowth of *C. difficile* spores have not previously been studied in depth, due in part to the absence of genetic tools. Specifically, the germination step, classically defined as the change in the optical density caused by spore rehydration and $Ca^{2+}$-DPA release, has not been studied as an independent phenomenon. Previous work showed that taurocholate, a bile salt, enhances colony formation by *C. difficile* spores recovered from environmental surfaces and stool. Bliss et al. (1997) *Diagn. Microbiol. Infect. Dis.* 29:1-4; Weese et al. (2000) *J. Vet. Diagn. Invest.* 12:449-452; Wilson et al. (1982) *J. Clin. Microbiol.* 15:443-446. Similarly, treatment of *C. difficile* spores with lysozyme and thioglycolate has been reported to enhance colony formation. Kamiya et al. (1989) *J. Med. Microbiol.* 28:217-221; Wilson (1983) *J. Clin. Microbiol.* 18:1017-1019. These effects on colony formation are clear, but it is difficult to discern what specific effects the treatments might have on germination.

Bile is produced by the liver and stored in the gall bladder. To aid in digestion, the gall bladder secretes bile into the duodenum, where it helps to absorb fat and cholesterol. The primary bile produced by the liver consists mainly of cholate and chenodeoxycholate conjugated with either taurine or glycine (FIG. 1). Ridlon et al. (2006) *J. Lipid Res.* 47:241-259. During passage through the distal ileum, bile is actively reabsorbed and recycled to the liver. However, 400 to 800 mg of bile passes daily from the ileum into the cecum, where it becomes a substrate for biotransforming reactions by the normal, benign bacterial flora. Thomas et al. (2001) *Gut* 49:835-842; Vlahcevic et al. (1996) In D. Zakim and T. Boyer (ed.), *Hepatology: a textbook of liver disease,* 3rd ed. W.B. Saunders Company, Philadelphia, Pa.

Many different species of bacteria, including *Clostridium perfringens*, express on their cell surfaces bile salt hydrolases (BSHs), which remove the conjugated amino acid from the primary bile salt. This hydrolysis reaction appears to proceed to completion, inasmuch as conjugated primary bile salts are essentially undetectable in the human cecum. Though some *Clostridium* species express BSHs, none have been described for *C. difficile*, and no open reading frame product with homology to BSHs in other species is present.

Unconjugated primary bile salts are taken up by a small percentage of bacterial species in the colon. Ridlon et al. (2006) *J. Lipid Res.* 47:241-259. One of these species, *Clostridium scindens*, actively transports unconjugated, primary bile salts into the cytosol and, through a series of enzymatic reactions, converts cholate and chenodeoxycholate to the secondary bile salts deoxycholate and lithocholate, respectively (FIG. 1). Mallonee et al. (1996) *J. Bacteriol.* 178:7053-7058; Wells et al. (2000) *Appl. Environ. Microbiol.* 66:1107-1113; White et al. (1980) *Steroids* 35:103-109. These secondary bile salts are secreted from the bacteria into the extracellular environment and are eventually excreted by the host.

As used herein, "*C. difficile*-associated disease" refers to any disease involving unwanted growth, toxin production, or tissue invasion in the bowel by *C. difficile*. *C. difficile*-associated diseases are well known in medicine and specifically include antibiotic-associated diarrhea (also known as *C. difficile* colitis), pseudomembranous colitis, and *C. difficile*-associated toxic megacolon. *C. difficile* colitis generally refers to profuse, watery diarrheal illness associated with the presence of at least one *C. difficile* toxin. Pseudomembranous colitis refers to a severe form of *C. difficile* colitis further characterized by bloody diarrhea, fever, and bowel wall invasion by *C. difficile*. Prior to the advent of tests to detect the *C.* difficile toxin, the diagnosis was most often made by colonoscopy or sigmoidoscopy. The appearance of "pseudomembranes" on the surface of the colon or rectum is diagnostic of the condition. The pseudomembranes are composed principally of inflammatory debris and white blood cells.

Compounds useful according to the invention are bile acids of Formula I

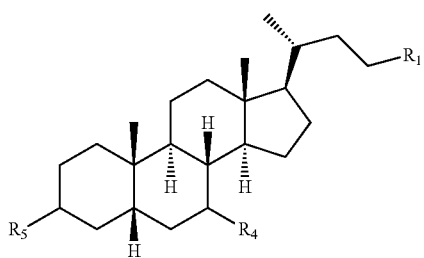

Formula I and pharmaceutically acceptable salts thereof, wherein:

$R_1$ is selected from the group consisting of —$CO_2H$, —$OC_2(R_2)$, —$CONH_2$, —$CON(R_2)_2$, —$CONHCH_2CH_2(R_3)$, —$CON(R_2)CH_2CH_2(R_3)$, —$NH_2$, —$NH(R_2)$, and —$N(R_2)_2$; and each of $R_4$ and $R_5$ is independently selected from the group consisting of —H, —$NH_2$, —$NH(R_2)$, —$N(R_2)_2$, —OH, —$O(R_2)$, and —OAcyl, wherein:

each $R_2$ is independently a straight or branched chain C1-C10 alkyl; and $R_3$ is selected from the group consisting of —$CO_2H$, —$SO_3H$, —$CONH_2$, —$SO_2NH_2$, —$OC_2(R_2)$, and —$SO_3(R_2)$.

In one embodiment $R_1$ is selected from the group consisting of —$CO_2H$, —$CONH_2$, —$CON(R_2)_2$, —$CONHCH_2CH_2(R_3)$, and —$CON(R_2)CH_2CH_2(R_3)$; and each of $R_4$ and $R_5$ is independently selected from the group consisting of —H, —OH, —$O(R_2)$, and —OAcyl.

In one embodiment $R_1$ is selected from the group consisting of —$NH_2$, —$NH(R_2)$, and —$N(R_2)_2$.

In one embodiment $R_4$ is selected from the group consisting of —$NH_2$, —$NH(R_2)$, and —$N(R_2)_2$.

In one embodiment $R_5$ is selected from the group consisting of —$NH_2$, —$NH(R_2)$, and —$N(R_2)_2$.

In one embodiment $R_1$ is —$OC_2(R_2)$, wherein $R_2$ is methyl; and each of $R_4$ and $R_5$ is —OAcyl, wherein Acyl is $C(=O)CH_3$.

In one embodiment $R_1$ is —$OC_2(R_2)$, wherein $R_2$ is methyl; and each of $R_4$ and $R_5$ is —OH.

In one embodiment $R_4$ is —OH.

In one embodiment each of $R_4$ and $R_5$ is —OH.

In one embodiment the compound of Formula I is chenodeoxycholate.

In one embodiment the compound of Formula I is ursodeoxycholate.

In one embodiment $R_1$ is —$CONHCH_2CH_2(R_3)$; $R_3$ is —$CO_2H$ or —$SO_3H$; $R_4$ is —OH; and $R_5$ is —OH.

In one embodiment $R_1$ is —$CON(R_2)CH_2CH_2(R_3)$; $R_2$ is methyl or ethyl; $R_3$ is —$CO_2H$ or —$SO_3H$; $R_4$ is —OH; and $R_5$ is —OH.

In one embodiment $R_1$ is —$CONHCH_2CH_2(R_3)$; $R_3$ is —$CO_2H$ or —$SO_3H$; $R_4$ is —H; and $R_5$ is —OH.

In one embodiment $R_1$ is —$CON(R_2)CH_2CH_2(R_3)$; $R_2$ is methyl or ethyl; $R_3$ is —$CO_2H$ or —$SO_3H$; $R_4$ is —H; and $R_5$ is —OH.

In one embodiment $R_1$ is —$CONHCH_2CH_2(R_3)$; each $R_2$ is independently a straight or branched chain C1-C10 alkyl; $R_3$ is selected from the group consisting of —$CONH_2$, —$SO_2NH_2$, and —$CO_2(R_2)$; and each of $R_4$ and $R_5$ is independently selected from the group consisting of —H, —OH, —$O(R_2)$, and —OAcyl.

In one embodiment $R_1$ is —$CON(R_2)CH_2CH_2(R_3)$; each $R_2$ is independently a straight or branched chain C1-C10 alkyl; $R_3$ is selected from the group consisting of —$CONH_2$ and —$SO_2NH_2$; and each of $R_4$ and $R_5$ is independently selected from the group consisting of —H, —OH, —$O(R_2)$, and —OAcyl.

In one embodiment $R_1$ is —$CON(R_2)CH_2CH_2(R_3)$; each $R_2$ is independently a straight or branched chain C1-C10 alkyl; $R_3$ is selected from the group consisting of —$SO_3(R_2)$ and —$OC_2(R_2)$; and each of $R_4$ and $R_5$ is independently selected from the group consisting of —H, —OH, —$O(R_2)$, and —OAcyl, wherein when $R_4$ is either —H or —OH, $R_5$ is selected from the group consisting of —H, —$O(R_2)$, and —OAcyl; and when $R_4$ is either —$O(R_2)$ or —OAcyl, $R_5$ is selected from the group consisting of —H, —OH, —$O(R_2)$, and —OAcyl.

As stated above, in addition to the individual compounds, pharmaceutically acceptable salts of each of the foregoing compounds are also useful according to the invention. Pharmaceutically acceptable salts are further disclosed below.

For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Diastereomers specifically include epimers, which are diastereomers that differ in configuration of only one stereogenic center.

Where an isomer/enantiomer or epimer is preferred, it may, in some embodiments, be provided substantially free of the corresponding enantiomer or epimer, and may also be referred to as "optically enriched." "Optically enriched," as used herein, means that the compound is made up of a significantly greater proportion of one enantiomer or epimer. In certain embodiments the compound of the present invention is made up of at least about 90% by weight of a preferred enantiomer or epimer. In other embodiments the compound is made up of at least about 95%, 98%, or 99% by weight of a preferred enantiomer or epimer. Preferred enantiomers or epimers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Ste-

*reochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

In the compounds and compositions of the invention, the term "alkyl" refers to the radical of aliphatic groups, including straight-chain alkyl groups and branched-chain alkyl groups, derived from a hydrocarbon moiety containing between one and twenty carbon atoms by removal of a single hydrogen atom. In certain embodiments, the term "alkyl" refers to the radical of saturated aliphatic groups, including straight-chain alkyl groups and branched-chain alkyl groups. In some embodiments, the alkyl group employed in the invention contains 1-20 carbon atoms. In certain embodiments, a straight chain or branched chain alkyl has 10 or fewer carbon atoms in its backbone (e.g., C1 to C10 for straight chain, C3 to C10 for branched chain), more preferably 6 or fewer, and even more preferably 4 or fewer. Examples of alkyl radicals include, but are not limited to, methyl, ethyl, n-propyl, iso-propyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like. Straight-chain alkyl groups specifically include methyl, ethyl, n-propyl, n-butyl, n-pentyl, n-hexyl, n-heptyl, n-octyl, n-nonyl, and n-decyl. The term "methyl" refers to the monovalent radical —$CH_3$. Branched-chain alkyl groups specifically include but are not limited to isopropyl, isobutyl, sec-butyl, tert-butyl, isopentyl, and isohexyl.

In certain embodiments, the term "alkyl" refers to an alkyl group bearing one or more substituents, i.e., a substituted alkyl group. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "aliphatic," as used herein, includes both saturated and unsaturated, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "cyano," as used herein, refers to a group of the formula (—CN).

The terms "halo" and "halogen" as used herein refer to an atom selected from fluorine (fluoro, —F), chlorine (chloro, —Cl), bromine (bromo, —Br), and iodine (iodo, —I).

"Hydroxy" or "hydroxyl" refers to the group —OH. "Alkoxy" refers to a group —OR, wherein R is an alkyl group as defined above. "Amino" refers to the group —$NH_2$. "Alkylamino" refers to a group —NHR or —NRR', where R and R' are independently chosen from alkyl or cycloalkyl groups as defined above.

"Acyl" refers to a group —C(=O)R, where R is H or alkyl, as defined above.

"Bile salts" comprise compounds which include cholate, lithocholate, deoxycholate, chenodeoxycholate, and ursodeoxycholate, which are shown below.

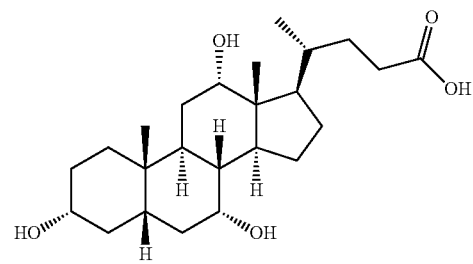

Cholate

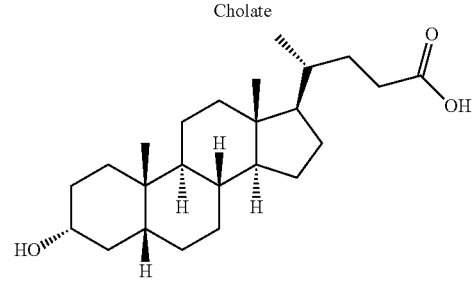

Lithocholate

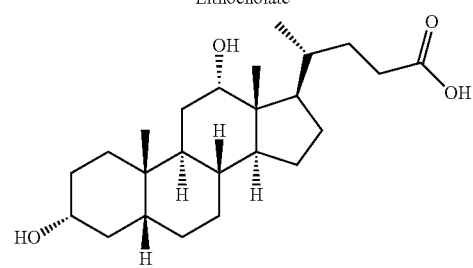

Deoxycholate

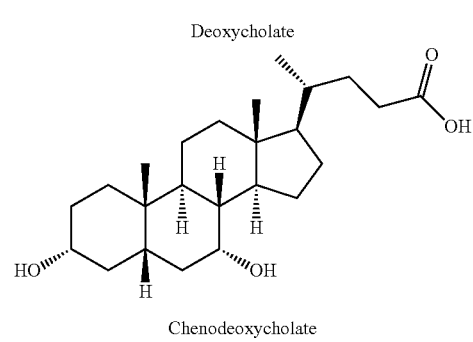

Chenodeoxycholate

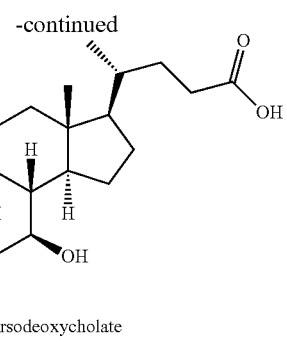

Ursodeoxycholate

As used herein, except as specified or may be required otherwise by context, the "bile salts" of the invention encompass both free carboxylic acids and the corresponding carboxylic acid salts, and vice versa. For example, the term "cholate" can refer to the free acid (cholic acid) as well as the corresponding carboxylic acid salt (cholate). Similarly, the term "lithocholate" can refer to the free acid (lithocholic acid) as well as the corresponding carboxylic acid salt (lithocholate). Likewise the term "chenodeoxycholate" can refer to the free acid (chenodeoxycholic acid) as well as the corresponding carboxylic acid salt (chenodeoxycholate). Without meaning to be limiting, the term "ursodeoxycholate" can refer to the free acid (ursodeoxycholic acid) as well as the corresponding carboxylic acid salt (ursodeoxycholate).

"Conjugation" of any of the bile salts, including but not limited to those shown above, implies a conversion of the carboxylate or carboxylic acid functionality to an amide peptide linkage derived from the amino group of glycine, taurine, or derivatives thereof. Likewise, "deconjugation" of the resulting amide linkage implies a cleavage or removal of glycine, taurine, or derivatives thereof, yielding the original bile salt carboxylic acid. Representative conjugations and deconjugations of chenodeoxycholate are shown below.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments, the present invention relates to a compound represented by any of the structures outlined herein, wherein the compound is a single stereoisomer.

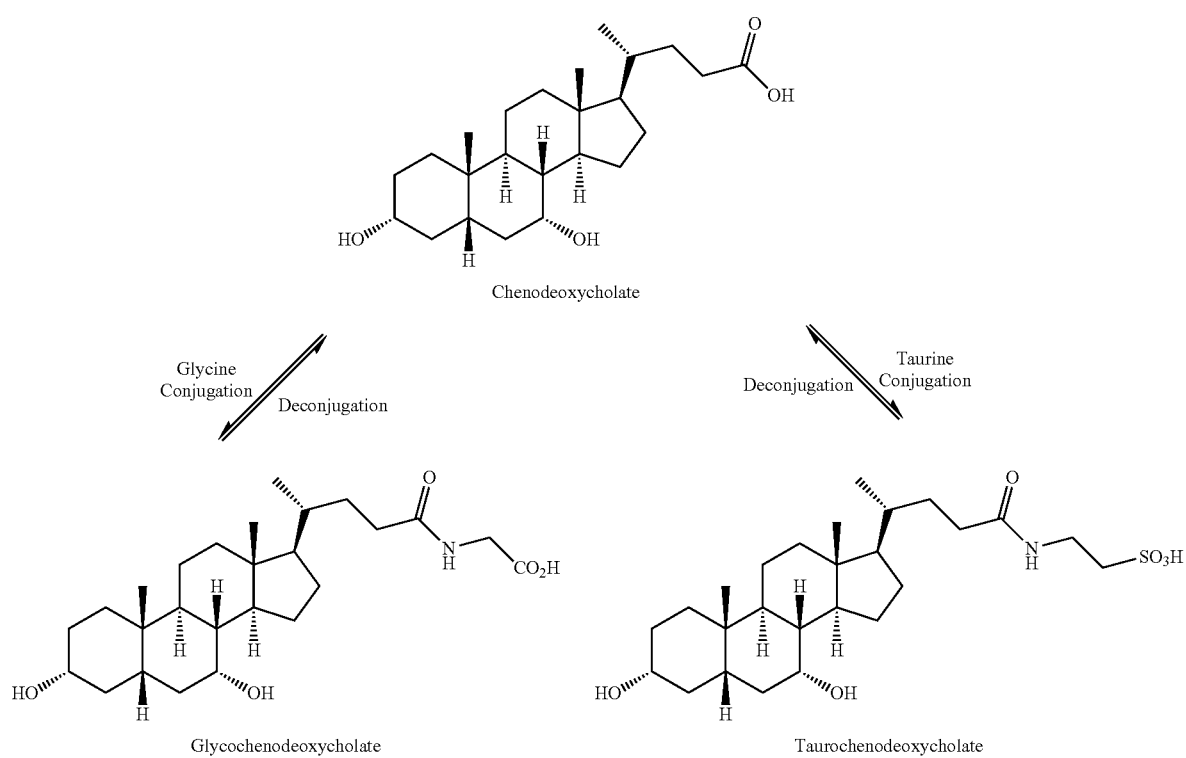

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Certain aspects of the invention are methods effective for prophylaxis against the development of C. difficile-associated disease in a mammalian subject at risk of developing C. difficile-associated disease. As used herein, a "subject at risk of developing C. difficile-associated disease" is a subject that is about to be exposed, that is exposed, or that has been exposed to at least one agent or condition associated with the development of C. difficile-associated disease but that has not yet developed C. difficile-associated disease. In one embodiment a "subject at risk of developing C. difficile-associated disease" is a subject that is about to be exposed, that is exposed, or that has been exposed to at least one agent or condition associated with the development of C. difficile colitis but that has not yet developed C. difficile colitis. In one embodiment a "subject at risk of developing C. difficile-associated disease" is a subject that is about to be exposed, that is exposed, or that has been exposed to at least one agent or condition associated with the development of pseudomembranous colitis but that has not yet developed pseudomembranous colitis.

As used herein, "at least one agent or condition associated with the development of C. difficile-associated disease" refers to antibiotics and antibiotic treatment associated with the development of C. difficile-associated disease. Antibiotics associated with the development of C. difficile-associated disease specifically include, without limitation, ampicillin, amoxicillin, clindamycin, fluoroquinolone antibiotics, and cephalosporin antibiotics.

Fluoroquinolone antibiotics specifically include, without limitation, balofloxacin, ciprofloxacin, difloxacin, enrofloxacin, fleroxacin, gatifloxacin, grepafloxacin, levofloxacin, lomefloxacin, marbofloxacin, moxifloxicin, nadifloxacin, norfloxacin, ofloxacin, orbifloxacin, pazufloxacin, perfloxacin, rufloxacin, sparfloxacin, temafloxacin, and tosufloxacin.

Cephalosporin antibiotics specifically include, without limitation, cefacetrile, cefaclomezine, cefaclor, cefadroxil, cefalexin, cefaloglycin, cefalonium, cefaloram, cefaloridine, cefalotin, cefaparole, cefapirin, cefatrizine, cefazaflur, cefazedone, cefazolin, cefbuperazone, cefcanel, cefcapene, cefclidine, cefdaloxime, cefdinir, cefditoren, cefedrolor, cefempidone, cefepime, cefetamet, cefetrizole, cefivitril, cefixime, cefluprenam, cefmatilen, cefmenoxime, cefmepidium, cefmetazole, cefminox, cefodizime, cefonicid, cefoperazone, cefoselis, cefotaxime, cefotetan, cefovecin, cefoxazole, cefoxitin, cefozopran, cefpimizole, cefpirome, cefpodoxime, cefprozil, cefquinome, cefradine, cefrotil, cefroxadine, cefsumide, ceftaroline, ceftazidime, cefteram, ceftezole, ceftibuten, ceftiofur, ceftiolene, ceftioxide, ceftizoxime, ceftriaxone, cefuracetime, cefuroxime, cefuzonam, and loracarbef.

A subject that is about to be exposed to at least one agent or condition associated with the development of C. difficile-associated disease is a subject that is expecting to be exposed to such agent or condition. For example, in one embodiment a subject that is about to be exposed to at least one agent or condition associated with the development of C. difficile-associated disease is a subject that is expecting to receive or be treated with an antibiotic associated with the development of C. difficile-associated disease.

A subject that is exposed to at least one agent or condition associated with the development of C. difficile-associated disease is a subject that is currently exposed to such agent or condition. For example, in one embodiment a subject that is exposed to at least one agent or condition associated with the development of C. difficile-associated disease is a subject that is currently receiving or being treated with an antibiotic associated with the development of C. difficile-associated disease.

A subject that has been exposed to at least one agent or condition associated with the development of C. difficile-associated disease is a subject that has been but is not currently exposed to such agent or condition. For example, in one embodiment a subject that has been exposed to at least one agent or condition associated with the development of C. difficile-associated disease is a subject that recently completed a course of treatment with an antibiotic associated with the development of C. difficile-associated disease. In one embodiment "recently completed" means that the subject concluded treatment with the antibiotic at least one day and up to sixty days prior to administration of a compound or composition according to the invention. In one embodiment "recently completed" means that the subject concluded treatment with the antibiotic at least one day and up to thirty days prior to administration of a compound or composition according to the invention. In one embodiment "recently completed" means that the subject concluded treatment with the antibiotic at least one day and up to fourteen days prior to administration of a compound or composition according to the invention. In one embodiment "recently completed" means that the subject concluded treatment with the antibiotic at least one day and up to seven days prior to administration of a compound or composition according to the invention.

Accordingly, in some embodiments the subject at risk of developing C. difficile-associated disease can be administered a compound of Formula I or a therapeutically acceptable salt thereof at the same time the subject is currently exposed to the at least one agent or condition associated with the development of C. difficile-associated disease. The dosing schedules for the compound of the invention and the agent associated with the development of C. difficile-associated disease can, but do not have to be, identical, provided they overlap.

In one embodiment, the administration of a compound of the invention can begin with or during the period in which the subject is exposed to at least one agent or condition associated with the development of C. difficile-associated disease and then continue beyond the period in which the subject is exposed to at least one agent or condition associated with the development of C. difficile-associated disease.

In one embodiment, the administration of a compound of the invention can begin up to 72 hours prior to the period during which the subject is exposed to at least one agent or condition associated with the development of C. difficile-associated disease and then continue through and beyond the period during which the subject is exposed to at least one agent or condition associated with the development of C. difficile-associated disease.

Certain aspects of the invention are methods effective for treatment of C. difficile-associated disease in a mammalian subject having a C. difficile-associated disease. As used herein, a "subject having C. difficile-associated disease" is a subject that has at least one objective manifestation of C. difficile-associated disease. In one embodiment a "subject having C. difficile-associated disease" is a subject that is suspected of having *C. difficile*-associated disease. In one embodiment a "subject having *C. difficile*-associated disease" is a subject that has been diagnosed as having *C. difficile*-associated disease. In one embodiment a "subject having *C. difficile*-associated disease" is a subject that has been diagnosed as having *C. difficile* colitis. In one embodiment a "subject having *C. difficile*-associated disease" is a subject that has been diagnosed as having pseudomembranous colitis but that has not yet developed pseudomembranous colitis.

In one embodiment a subject having *C. difficile*-associated disease is a subject that is currently exposed to at least one agent or condition associated with the development of *C. difficile*-associated disease. For example, in one embodiment a subject having *C. difficile*-associated disease is a subject that is currently receiving at least one antibiotic associated with the development of *C. difficile*-associated disease.

In one embodiment a subject having *C. difficile*-associated disease is a subject that was recently exposed to at least one agent or condition associated with the development of *C. difficile*-associated disease. For example, in one embodiment a subject having *C. difficile*-associated disease is a subject that recently received at least one antibiotic associated with the development of *C. difficile*-associated disease. In one embodiment "recently received" means that the subject concluded treatment with the antibiotic at least one day and up to sixty days prior to administration of a compound or composition according to the invention. In one embodiment "recently received" means that the subject concluded treatment with the antibiotic at least one day and up to thirty days prior to administration of a compound or composition according to the invention. In one embodiment "recently received" means that the subject concluded treatment with the antibiotic at least one day and up to fourteen days prior to administration of a compound or composition according to the invention. In one embodiment "recently received" means that the subject concluded treatment with the antibiotic at least one day and up to seven days prior to administration of a compound or composition according to the invention.

A subject having a *C. difficile*-associated disease can receive a compound of the invention concurrently with another agent suitable for treatment of the *C. difficile*-associated disease. For example, the subject can be administered a compound of the invention and an antibiotic such as vancomycin or metronidazole in order to treat the *C. difficile*-associated disease. The dosing schedules for the compound of the invention and the other agent suitable for treating *C. difficile*-associated disease can, but do not have to be, identical, provided they overlap.

Other Indications for Bile Salts

Ursodeoxycholic acid, other bile acids, and salts thereof are sometimes administered to subjects to treat conditions other than *C. difficile*-associated disease, including bile salt deficiency, liver disease, gallstones, gastrointestinal complications associated with cystic fibrosis, alcohol-induced hangover, drug toxicity, colon cancer following gallbladder surgery, and deficiency associated with poor digestion of fats and lipids in the intestine. U.S. Pat. No. 5,415,872. The usual oral dosage of ursodeoxycholic acid for such conditions is 2 to 15 mg/kg body weight once or twice per day. Higher doses of ursodeoxycholic acid have sometimes been associated with undesirable side effects including diarrhea.

In one embodiment of the invention the subject is free of such conditions, other than *C. difficile*-associated disease, for which a bile acid or salt thereof is indicated for the treatment of such conditions. That is, in one embodiment the subject of the invention is otherwise free of bile salt deficiency, liver disease, gallstones, gastrointestinal complications associated with cystic fibrosis, alcohol-induced hangover, drug toxicity, colon cancer following gallbladder surgery, and deficiency associated with poor digestion of fats and lipids in the intestine.

In one embodiment of the invention the subject is free of other conditions, aside from being at risk of developing *C. difficile*-associated disease, for which a bile acid or salt thereof is indicated for the treatment of such other conditions. That is, in one embodiment the subject of the invention is at risk of developing *C. difficile*-associated disease but is otherwise free of bile salt deficiency, liver disease, gallstones, gastrointestinal complications associated with cystic fibrosis, alcohol-induced hangover, drug toxicity, colon cancer following gallbladder surgery, and deficiency associated with poor digestion of fats and lipids in the intestine.

In various embodiments of the invention a bile acid or salt thereof of the invention is administered solely for the purpose of preventing *C. difficile*-associated disease, reducing the risk of developing *C. difficile*-associated disease, or treating *C. difficile*-associated disease.

Formulations —Single or Combination

In one embodiment the bile acid or salt thereof of the invention is a single bile acid or salt thereof. For example, in one embodiment the compound of Formula I to be administered to a subject is chenodeoxycholic acid or a salt thereof and essentially no other bile acid or salt thereof.

In one embodiment the bile acid or salt thereof of the invention is formulated so as to include predominantly a single bile acid or salt thereof. According to this embodiment the single bile acid or salt thereof accounts for at least 75 percent, at least 80 percent, at least 85 percent, at least 90 percent, or at least 95 percent of a particular bile salt formulation. For example, in one embodiment the compound of Formula I to be administered to a subject is at least 80 percent chenodeoxycholic acid or a salt thereof. As another example, in one embodiment the compound of Formula I to be administered to a subject is at least 95 percent chenodeoxycholic acid or a salt thereof.

In one embodiment the bile acid or salt thereof of the invention is formulated as a combination of bile acids or salts thereof. For example, in one embodiment the compound of Formula I to be administered to a subject includes chenodeoxycholic acid or a salt thereof and at least one additional bile acid or salt thereof. For example, in one embodiment the compound of Formula I to be administered to a subject includes chenodeoxycholic acid or a salt thereof and ursodeoxycholic acid or a salt thereof. The bile acid or salt thereof can include two, three, four, five, six, or more bile acids and salts thereof.

In various embodiments of the invention a compound of the invention is administered to a subject solely for the purpose of preventing *C. difficile*-associated disease, reducing the risk of developing *C. difficile*-associated disease, or treating *C. difficile*-associated disease.

Antigerminants

Various aspects of the invention are methods that entail inhibition of germination of *C. difficile* spores, including in vivo. As mentioned above, it has now been discovered that certain bile acids, for example the compounds of Formula I, and salts thereof inhibit germination of *C. difficile* spores. As used herein, "to inhibit germination of *C. difficile* spores" means to reduce germination of *C. difficile* spores by a measurable amount or measurable extent compared to control. The measurable amount or measurable extent can but need not necessarily be complete or 100 percent. For example, in one embodiment "to inhibit germination of *C. difficile* spores" means to reduce germination of *C. difficile* spores by at least 10 percent compared to control. In other embodiments "to inhibit germination of *C. difficile* spores" means to reduce germination of *C. difficile* spores by at least 20 percent, at least 30 percent, at least 40 percent, at least 50 percent, at least 60 percent, at least 70 percent, at least 80 percent, or at least 90 percent compared to control.

Various aspects of the invention are methods that entail inhibition of growth of *C. difficile*, including in vivo. As mentioned above, it has now been discovered that certain bile acids, for example the compounds of Formula I, and salts thereof inhibit germination of *C. difficile* spores. Also as mentioned above, by inhibiting spore germination it is also possible to inhibit downstream generation and growth of the vegetative state of *C. difficile*. Furthermore, certain compounds with antigerminant activity are also capable of inhibiting the vegetative growth of *C. difficile*. For example, chenodeoxycholate and ursodeoxycholate, in addition to being antigerminants of *C. difficile*, are also capable of inhibiting the vegetative growth of *C. difficile*. As used herein, "to inhibit growth of *C. difficile*" means to reduce growth of *C. difficile* by a measurable amount or measurable extent compared to control. The measurable amount or measurable extent can but need not necessarily be complete or 100 percent. For example, in one embodiment "to inhibit growth of *C. difficile*" means to reduce growth of *C. difficile* by at least 10 percent compared to control. In other embodiments "to inhibit growth of *C. difficile*" means to reduce growth of *C. difficile* by at least 20 percent, at least 30 percent, at least 40 percent, at least 50 percent, at least 60 percent, at least 70 percent, at least 80 percent, or at least 90 percent compared to control.

Many of the bile salts described herein, such as chenodeoxycholate, and the conjugating reagents, such as taurine and sarcosine methyl ester, are commercially available from suppliers such as Sigma-Aldrich, which offers the following: sodium chenodeoxycholate (CAS No.: 2646-38-0; Sigma-Aldrich catalog #C8261); ursodeoxycholic acid (Sigma-Aldrich catalog #U 5127); sodium cholate (CAS No.: 206986-87-0; Sigma-Aldrich catalog #270911); sodium deoxycholate (CAS No.: 302-95-4; Sigma-Aldrich catalog #D6750); taurine (CAS No.: 107-35-7; Sigma-Aldrich catalog #T0625); sarcosine methyl ester HCl (CAS No.: 13515-93-0; Sigma-Aldrich catalog #84570).

Additional bile salts that may be useful according to the invention are commercially available from additional suppliers such as Steraloids Inc. (Newport, R.I.) and VWR (West Chester, Pa.). For example, the following compounds are available from Steraloids Inc.: 5β-cholanic acid n-(2-sulphoethyl)-amide (catalog no. C0835-000); 5β-cholanic acid-3α, 7α-diol 3-acetate methyl ester (catalog no. C0950-000); 5β-cholanic acid-3α,7α-diol diacetate methyl ester (5β-cholan-24-oic acid-3α,7α-diol methyl ester 3,7-diacetate) (CAS No. 2616-71-9; catalog no. C0964-000); 5β-cholanic acid-3α,7α-diol methyl ester (catalog no. C0975-000); and 5β-cholanic acid-3α,7β-diol methyl ester (ursodeoxycholic acid methyl ester) (catalog no. C1040-000). The following compounds are available from VRW: ursodeoxycholic acid (CAS No. 128-13-2; catalog no. B20490-03); ursodeoxycholic acid, sodium salt (catalog no. 104626); chenodeoxycholic acid (catalog no. 22877-0050); and tauroursodeoxycholic acid, sodium salt (CAS No. 14605-22-2; catalog no. 002161).

Identification and Development of Lead Compounds

Starting with an initial active compound such as chenodeoxycholic acid (CDCA), a collection of commercially available structurally related but diverse compounds can be obtained for structure-activity relationship (SAR) studies. This initial commercial library can be used to probe SAR and develop a model to direct further synthesis efforts. Based on the model, several iterative rounds of medicinal chemistry on small libraries around the general hit can be performed in an attempt to increase biological activity and decrease unwanted potential toxicological and physico-chemical properties. Initial attempts focus on improving the biological activity and generating an SAR trend, as well as identifying points on the general hit structures for additional interactions with the target. In the process of this initial work, attempts can be made to identify the minimum pharmacophore needed for activity and to obtain a broad sense of SAR.

After the initial library sets are tested, the biological activity information can be used to rank each chemistry modification and to begin constructing an SAR trend of each of the library series. Using this information, a second series of compounds can be prepared to refine the SAR trend. In addition, specific concerns such as activity, solubility, ADME (absorption, distribution, metabolism, excretion), or the like, can be addressed when and if they arise.

Several iterations of this synthesis-testing-synthesis protocol may be needed to address all the issues and generate a potent, selective inhibitor with an appropriate pharmacokinetic (PK) profile. While many of these issues can be adjusted simultaneously, when this is not possible, the general priority can be: first, removal of obvious problematic functionality; second, modification of the core chemical structure for ease of medicinal chemistry; third, increase of potency; and fourth, all other issues. These are general guidelines which may be modified as the program develops based on information learned in the process.

Parallel to the synthetic chemistry efforts, a continued effort may be undertaken to search for any commercially available compounds structurally similar to CDCA as well as the proposed libraries. Compounds that fit the criteria can be purchased and tested. Information gained through this channel can be used to refine the SAR model and to help direct synthesis toward more promising structures.

Ultimately, each library series typically will reach a go/no-go decision point where, based on selected criteria, the compounds will be progressed, put on hold, or dropped. In the end only one series may be progressed to pre-clinical candidate stage based on all the data acquired to that point.

Establishing criteria for compound evaluation including in vivo activity, in vitro activity, and PK and ADME thresholds can be accomplished in a similar manner as described above. Existing data, closely related analogs, and any previous literature precedent can be used to define acceptable values for these metrics. In preferred embodiments, biological activity should ultimately reach the sub-micromolar range and PK/ADME should be comparable to any known drugs.

Go/no-go decisions may be based on an aggregate of all the above criteria, as well as understanding of SAR, chemical feasibility, and any early toxicity data available. These metrics may also be reached by consensus as described above.

$R_1$, $R_4$, and $R_5$ of Formula I as disclosed herein correspond to three structural parts of chenodeoxycholic acid that may be systematically investigated in order to generate specific SAR and identify the minimum pharmacophore responsible for biological activity.

Many commercially available CDCA analogs possess more than a single structural change and thus can furnish a broad sense of SAR. The broad SAR generated through testing a large number of commercially available CDCA analogs can be used to guide the future synthesis of specific analogs.

For testing purposes, assays should, in general, be reproducible and should not be changed after the beginning of the project. Positive and negative controls should be run each time. If the controls do not fall within the predefined range, all data from that run should be considered suspect.

Ideally the primary screen should measure the direct desired interaction between the compound and its target in a system isolated from as many external factors as possible. For example, testing can proceed via the spore germination assay and/or the colony formation assay described herein. Primary screens may be run at a single concentration, although running a limited number of concentrations is also possible. Ultimately the goal is to be able to rapidly and inexpensively test a large number of compounds to quickly eliminate compounds which have little chance of progressing and focus on those with the highest probability of success. If only one assay is used for initial testing, hits should be tested in a secondary assay for confirmatory purposes. Results from all assays are compared and, based on predetermined criteria, hits (i.e., lead compounds) are defined.

Hits from the primary assay may be validated in a secondary assay by measuring their dose response. This can be in the form of, for example, an $IC_{50}$, $EC_{50}$, or minimum inhibitory concentration (MIC). This is an important step since it serves to eliminate compounds which are non-specific binders or detergent-like. A good sigmoidal shape to the inhibition curve is indicative of a valid dose response. $IC_{50}$ ($EC_{50}$) criteria may be established for progressing further.

Validated hits can be screened in a selectivity assay to determine off-target activity or cross-reactivity against similar targets. This selectivity assay can be set up in a similar manner to the primary screening assay. Review of the literature may assist to define any potential off-target reactivity. Criteria for selectivity may be established for progressing further.

Solubility of selected compounds may be determined, for example using a turbidometric assay, to ensure that they do not precipitate on dilution in media. Note that this assay can be done earlier if solubility is deemed to be a problem for any of the earlier assays.

Probiotic

Certain aspects of the invention relate to a probiotic comprising at least one strain of bacteria that is capable of metabolizing primary bile salts to secondary bile salts. Bile acids formed by synthesis in the liver are termed "primary" bile acids, and those made by bacteria are termed "secondary" bile acids. As a result, chenodeoxycholic acid is a primary bile acid, and lithocholic acid is a secondary bile acid. In humans, taurocholic acid and glycocholic acid, both primary bile acids, normally account for approximately 80 percent of all bile acids. Deoxycholate (also known as desoxycholate), a secondary bile acid, has been reported to promote spore germination but also to inhibit growth of *C. difficile*. Wilson (1983) *J. Clin. Microbiol.* 18:1017-1019; Sorg et al. (2008) *J. Bacteriol.* 190:2505-2512.

As used herein, "probiotics" are microbial cell preparations that have a beneficial effect on the health and well-being of the host. This definition includes microbial cells but not isolated metabolites of such microbial cells, such as certain antibiotics. Probiotics, which are introduced into the gastrointestinal tract, can influence gastrointestinal microflora and play a beneficial role in the host.

Without meaning to be bound by any particular theory or mechanism of action, it is the belief of the inventors that antibiotic therapy can cause *C. difficile*-associated disease by killing off bowel flora that are responsible for the conversion of primary bile acids to germination-inhibiting and/or growth-inhibiting secondary bile acids, thereby permitting *C. difficile* germinants entering the anaerobic environment of the colon to colonize and reproduce *C. difficile* in its vegetative state. Thus, alternatively or in addition to administering an anti-germinant such as a compound of Formula I and salts thereof, it is possible to limit growth of *C. difficile* in its vegetative state by administering a probiotic comprising at least one strain of bacteria that is capable of metabolizing primary bile salts to secondary bile salts.

Strains of bacteria that are capable of metabolizing primary bile salts to secondary bile salts include *Clostridium scindens*, *Clostridium leptum* (ATCC 29065), and *Clostridium hiranonis* (also known as TO931). *C. scindens* (ATCC 35704) and *C. leptum* (ATCC 29065) can be obtained from American Type Culture Collection of Manassas, Va. *C. hiranonis* (TO931) may be obtained as described in Wells J E et al. (2003) *Clin. Chim. Acta.* 331:127-34, or from Professor Phillip B. Hylemon of Virginia Commonwealth University.

In one embodiment of the present invention, a therapeutic composition comprising at least one strain of bacteria that is capable of metabolizing primary bile salts to secondary bile salts, e.g., *C. scindens*, in a pharmaceutically-acceptable carrier suitable for oral administration to the gastrointestinal tract of a human or animal, is provided. In another embodiment, at least one strain of bacteria that is capable of metabolizing primary bile salts to secondary bile salts, e.g., *C. scindens*, is included in the therapeutic composition in the form of spores. In another embodiment, at least one strain of bacteria that is capable of metabolizing primary bile salts to secondary bile salts, e.g., *C. scindens*, is included in the composition in the form of a dried or lyophilized cell mass.

The inventive probiotic formulation may be administered as a food supplement. Such a formulation may contain conventional fillers and extenders such as, for example, rice flour. Conveniently, the probiotic formulation may be taken orally. In one embodiment, the dosage rate, effective as a food supplement and for maintaining or reestablishing beneficial bacteria in the intestinal tract, ranges from about 5 milligrams to about 4000 milligrams per day.

The bacteria can be provided as spores or as vegetative bacteria, provided they are viable. Typical dosing will include $1 \times 10^3$ to $1 \times 10^{14}$ viable, vegetative bacteria or spores per day.

In one embodiment, the bacteria are present in the probiotic composition at a concentration of approximately $1 \times 10^3$ to $1 \times 10^{14}$ colony forming units (CFU)/gram, preferably approximately $1 \times 10^5$ to $1 \times 10^{12}$ CFU/gram, whereas in other preferred embodiments the concentrations are approximately $1 \times 10^9$ to $1 \times 10^{13}$ CFU/gram, approximately $1 \times 10^5$ to $1 \times 10^7$ CFU/g, or approximately $1 \times 10^8$ to $1 \times 10^9$ CFU/gram.

In one embodiment a sufficient amount of the bacteria is administered to achieve at least a normal amount of said bacteria in the bowel.

U.S. Pat. No. 5,733,568 teaches the use of microencapsulated *Lactobacillus* bacteria for treatment of antibiotic associated or other acute and chronic diarrhea as well as for skin and vaginal yeast infections. The microencapsulation is said to prevent inactivation of the *bacillus* and to deliver it to the intestine as well as to avoid lactose intolerance seen in said diarrheas.

Pharmaceutical compositions of the present invention are preferably enteric coated or microencapsulated for delivery to the desired regions of the bowel of a patient in need thereof. Enteric coating of the composition is specifically designed to deliver the sorbents and bacterial source at desired regions of the bowel where conversion of primary bile acids to secondary bile acids can occur. This is preferably achieved via an enteric coating material that disintegrates and dissolves at a pH of 7.5 or higher. Examples of enteric coatings with these characteristics include, but are not limited to, Zein, polyglycolactic acid, polylactic acid, polylactide-co-glycolide and similar coating materials.

Alternatively, dry probiotic formulations can be prepared which are stable and resistant to gastric juice at pH 1.5 to 2.5; and to reduce the water in the production process so it does not reduce the shelf-life of the formulations. Such formulations can be prepared in a low humidity room with relative humidity controlled at 20% (+/−5%). One can use a vacuum drier (e.g., LabLine Model #3620, from Lab-Line Instruments, Inc., Melrose Park, Ill.) which is capable of drying powders in trays at temperatures from about 40 to 70° C., at vacuums ranging from 24 to 29 inches of Hg.

Suitable liquid or gel-based carriers are well-known in the art (e.g., water, physiological salt solutions, urea, methanol, ethanol, propanol, butanol, ethylene glycol and propylene glycol, and the like). Preferably, water-based carriers are approximately neutral pH.

In one embodiment, oral delivery of the composition is accomplished via a 2 to 4 ounce emulsion or paste mixed with an easy to eat food such as a milk shake or yogurt. The microencapsulated bacterial probiotic can be administered along with other pharmaceutically active agents or separately, for example in a swallowable gelatin capsule or tablet.

In various embodiments of the invention a probiotic of the invention is administered solely for the purpose of preventing *C. difficile*-associated disease, reducing the risk of developing *C. difficile*-associated disease, or treating *C. difficile*-associated disease.

Because the probiotic includes at least one strain of bacteria, the probiotic will generally be administered in absence of concurrent administration of an antibiotic that would kill or otherwise inhibit reproduction of the probiotic bacteria in the digestive tract of the subject. For example, a subject at risk of developing *C. difficile*-associated disease may be administered a probiotic of the invention after completing a course of antibiotic therapy that is associated with the development of *C. difficile*-associated disease. As another example, a subject having *C. difficile*-associated disease may be administered a probiotic of the invention after completing a course of antibiotic therapy that is associated with the development of *C. difficile*-associated disease.

In one embodiment a method of the invention for preventing *C. difficile*-associated disease in a subject includes administering to the subject both a compound of the invention and a probiotic of the invention. The compound of the invention and the probiotic of the invention can be given concurrently or sequentially in either order. The dosing schedules for the compound of the invention and the probiotic of the invention can but do not have to be identical, provided they overlap. As noted above, the probiotic will generally be administered in absence of concurrent administration of an antibiotic that would kill or otherwise inhibit reproduction of the probiotic bacteria in the digestive tract of the subject.

In one embodiment a method of the invention for treating *C. difficile*-associated disease in a subject includes administering to the subject both a compound of the invention and a probiotic of the invention. The compound of the invention and the probiotic of the invention can be given concurrently or sequentially in either order. The dosing schedules for the compound of the invention and the probiotic of the invention can but do not have to be identical, provided they overlap. As noted above, the probiotic will generally be administered in absence of concurrent administration of an antibiotic that would kill or otherwise inhibit reproduction of the probiotic bacteria in the digestive tract of the subject.

Pharmaceutically Acceptable Salts

As set out herein, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, phosphonate, nitrate, acetate, valerate, oleate, palmitate, stearate, laurate, benzoate, lactate, tosylate, citrate, maleate, fumarate, succinate, tartrate, napthylate, mesylate, glucoheptonate, lactobionate, and laurylsulphonate salts and the like. See, for example, Berge et al. (1977) *J. Pharm. Sci.* 66:1-19.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, for example, Berge et al. (1977) *J. Pharm. Sci.* 66:1-19.

Drug Formulations

Compositions useful in the practice of this invention can be formulated as pharmaceutical compositions together with pharmaceutically acceptable carriers for parenteral administration or enteral administration or for topical or local administration. For example, the compositions useful in the practice of the invention can be administered as oral formulations in solid or liquid form, or as intravenous, intramuscular, subcutaneous, transdermal, or topical formulations. Oral formulations for local delivery are preferred.

The compounds and compositions are typically administered with pharmaceutically acceptable carriers. The term "pharmaceutically-acceptable carrier" as used herein means one or more compatible solid, or semi-solid or liquid fillers, diluants or encapsulating substances which are suitable for administration to a human or other mammal such as a dog, cat, horse, cow, sheep, or goat. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral and rectal formulations can be found in Remington's Pharmaceutical Sciences, Mack Publishing Company, Easton, Pa.

Pharmaceutically acceptable carriers for oral administration include capsules, tablets, pills, powders, troches, and granules. In the case of solid dosage forms, the carrier can comprise at least one inert diluent such as sucrose, lactose or starch. Such carriers can also comprise, as is normal practice, additional substances other than diluents, e.g. lubricating agents such as magnesium stearate. In the case of capsules, tablets, troches and pills, the carrier can also comprise buffering agents. Carriers, such as tablets, pills and granules, can be prepared with coatings on the surfaces of the tablets, pills or granules which control the timing and/or the location of release of the pharmaceutical compositions in the gastrointestinal tract. In some embodiments, the carriers also target the active compositions to particular regions of the gastrointestinal tract and even hold the active ingredients at particular regions, such as is known in the art. Alternatively, the coated compounds can be pressed into tablets, pills, or granules. Pharmaceutically acceptable carriers include liquid dosage forms for oral administration, e.g. emulsions, solutions, suspensions, syrups and elixirs containing inert diluents commonly used in the art, such as water. Besides such inert diluents, compositions can also include additional inactive components such as wetting agents, emulsifying and suspending agents, and sweetening and other flavoring agents.

The pharmaceutical preparations of the invention may be provided in particles. Particles as used herein means nano- or microparticles (or in some instances larger) which can consist in whole or in part of the peripheral opioid antagonists or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the antagonist in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

When used in its acid form, a compound of the present invention can be employed in the form of a pharmaceutically acceptable salt of the acid. Carriers such as solvents, water, buffers, alkanols, cyclodextrins and aralkanols can be used. Other auxiliary, non-toxic agents may be included, for example, polyethylene glycols or wetting agents.

The pharmaceutically acceptable carriers and compounds described in the present invention are formulated into unit dosage forms for administration to the patients. The dosage levels of active ingredients (i.e. compounds of the present invention) in the unit dosage may be varied so as to obtain an amount of active ingredient that is effective to achieve a therapeutic effect in accordance with the desired method of administration. The selected dosage level therefore mainly depends upon the nature of the active ingredient, the route of administration, and the desired duration of treatment. If desired, the unit dosage can be such that the daily requirement for an active compound is in one dose, or divided among multiple doses for administration, e.g. two to four times per day.

The pharmaceutical preparations of the invention, when used in alone or together with other agents including antibiotics, are administered in therapeutically effective amounts. A therapeutically effective amount will be that amount which establishes a level of the drug(s) effective for treating a subject, such as a human subject. An effective amount means that amount, alone or with multiple doses, necessary to achieve a desired biological effect. When administered to a subject, effective amounts will depend, of course, on the particular effect chosen as the end-point; the severity of the condition being treated; individual patient parameters including age, physical condition, and weight; concurrent treatment; frequency of treatment; and the mode of administration. These factors are well known to those of ordinary skill in the art and can be addressed with no more than routine experimentation.

Routes of Delivery

In general, the compounds and compositions employed in the methods of the invention can be administered enterally. In one embodiment compounds and compositions employed in the methods of the invention can be administered orally. In one embodiment compounds and compositions employed in the methods of the invention can be administered rectally.

The active ingredient may be administered once, or it can be divided into a number of smaller doses to be administered at intervals of time. It is understood that the precise dosage and duration of treatment is a function of the disease being treated and may be determined empirically using known testing protocols or by extrapolation from in vivo or in vitro test data. For example, the dosage and duration of treatment can be determined by extrapolation from in vivo data obtained using one or more animal models of *C. difficile*-associated disease. It is to be noted that concentrations and dosage values may also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed invention.

If oral administration is desired, the active compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other ingredient that is protective against the acidic environment of the stomach.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Enteric coated tablets are well known to those skilled in the art. In addition, capsules filled with small spheres each coated to protect from the acidic stomach, are also well known to those skilled in the art.

The oral dosage forms generally are administered to the patient one to four times daily. It is preferred that the compounds employed in the methods of the invention be administered either three or fewer times a day, more preferably once or twice daily.

When administered orally, an administered amount therapeutically effective to inhibit spore germination or to inhibit growth is from about 1 mg/kg body weight/day to about 100 mg/kg body weight/day. In one embodiment the oral dosage is from about 1 mg/kg body weight/day to about 50 mg/kg body weight/day. In one embodiment the oral dosage is from about 5 mg/kg body weight/day to about 50 mg/kg body weight/day. It is understood that while a patient may be started at one dose, that dose may be varied over time as the patient's condition changes.

Pharmaceutical formulations adapted for "rectal administration" may be presented as suppositories or as enemas. These formulations which are presented as suppositories can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

As used herein, a "subject" is defined as a mammal and illustratively includes humans, non-human primates, horses, goats, cows, sheep, pigs, dogs, cats, and rodents. In one embodiment a subject is a human.

The present invention is further illustrated by the following examples, which in no way should be construed as further limiting. The entire contents of all of the references (including literature references, issued patents, published patent applications, and co-pending patent applications) cited throughout this application are hereby expressly incorporated by reference.

EXAMPLES

Strains and Growth Conditions.

*C. difficile* CD196 and *C. perfringens* SM101 were described previously. Popoff et al. (1988) *Infect. Immun.* 56:2299-2306; Zhao et al. (1998) *J. Bacteriol.* 180:136-142. *C. difficile* UK14 was isolated during the epidemic *C. difficile* outbreak at Stoke-Mandeville Hospital, Aylesbury, Buckinghamshire, England (Meridian Biosciences strain number SM8-6865). All strains were grown in BHIS (brain heart infusion [Difco] supplemented with yeast extract [5 mg/ml] and L-cysteine [0.1%]) at 37° C. under anaerobic conditions in a Coy Laboratory anaerobic chamber.

Preparation of *C. difficile* Spores.

Sporulation of *C. difficile* was induced on BHIS agar as described previously. Haraldsen et al. (2003) *Mol. Microbiol.* 48:811-821. Briefly, an overnight *C. difficile* culture in BHIS medium was diluted in fresh medium to an optical density at 600 nm ($OD_{600}$) of 0.2. A 150-µl portion of this suspension was spread on 5 ml BHIS agar in each well of a six-well tissue culture dish. The culture was incubated anaerobically for 4 to 7 days. To determine spore colony formation, samples from the plates containing mixed populations of spores and vegetative cells were resuspended in BHIS and heated to 60° C. for 20 min to kill vegetative cells before cooling, diluting, and plating on BHIS medium. For use in germination assays, spores were purified by a method similar to that described by Akoachere and colleagues. Akoachere et al. (2007) *J. Biol. Chem.* 282:12112-12118. The vegetative cell-spore mixture was collected by flooding each well of the six-well dish with ice-cold sterile water. After five washes with ice-cold water, the bacteria were suspended in 20% (wt/vol) HistoDenz (Sigma, St. Louis, Mo.). This suspension was layered onto a 50% (wt/vol) HistoDenz solution in a centrifuge tube, and the tube was centrifuged at 15,000×g for 15 min to separate spores from vegetative cells. The purified spores, collected at the bottom of the centrifuge tube, were washed twice with ice-cold water to remove traces of HistoDenz and resuspended in water.

In Vitro Response of *C. difficile* Spores to Bile Salts.

To determine the response time of *C. difficile* spores to taurocholate, spores were prepared as described above. Vegetative bacteria were heat killed by incubation for 20 min at 60° C. The heat-treated spores were washed three times in water to remove traces of nutrients and returned to the anaerobic chamber to allow subsequent colony formation. Spores were resuspended in water, and either taurocholate, glycocholate, cholate, deoxycholate, ursodeoxycholate, or chenodeoxycholate (Sigma, St. Louis, Mo.) was added to 0.1%. At various times, samples were removed, serially diluted, and plated on BHIS agar. One sample was removed prior to the addition of taurocholate and spread on BHIS and BHIS(TA) (BHIS plus 0.1% taurocholate). The latter platings served as negative and positive controls for colony formation, respectively. After overnight growth, colonies were enumerated (colony forming units, CFU), and the number was compared to that obtained on BHIS(TA).

To determine the amount of taurocholate needed to induce colony formation by *C. difficile* spores, spores were prepared, heated, and washed as described above. Heat-treated *C. difficile* spores were resuspended in water containing various concentrations of taurocholate. After a 10-minute incubation, the suspensions were serially diluted in BHIS and plated on BHIS agar. After overnight growth, colonies were enumerated, and the number was compared to that obtained by overnight growth on BHIS(TA).

Germination of *C. difficile* Spores.

Germination of *C. difficile* spores was measured by diluting purified *C. difficile* spores to an $OD_{600}$ of 0.3 to 0.4 in BHIS alone or BHIS containing 1% bile salts (taurocholate, glycocholate, cholate, or deoxycholate). For experiments in complete defined medium, a mixture of salts [0.3 mM $(NH_4)_2SO_4$, 6.6 mM $KH_2PO_4$, 15 mM NaCl, 59.5 mM $NaHCO_3$, and 35.2 mM $Na_2HPO_4$] was used to buffer the spores and putative germinants. Karlsson et al. (1999) *Microbiology* 145:1683-1693. The $OD_{600}$ was determined immediately (time zero) and at various time points during incubation at room temperature. The ratios of the optical densities at the various time points to the optical density at time zero were plotted against time.

Statistical Analysis.

All assays listed above were performed in triplicate, and data are reported as means and standard deviations from three independent experiments.

Example 1

Figure 2:
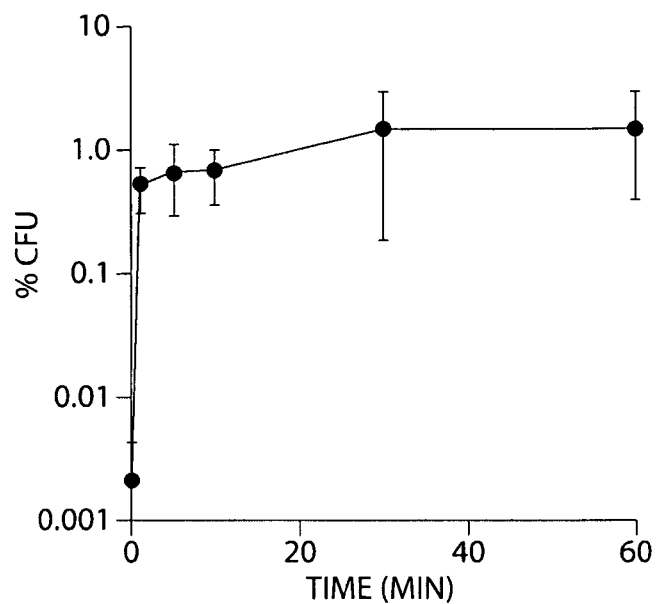
FIG. 2 is a graph depicting rate of response of C. difficile spores to taurocholate as a function of duration of exposure. C. difficile spores were suspended in water containing 0.1% taurocholate. At 1, 5, 10, 30, and 60 min, spores were serially diluted and plated on BHIS agar in the absence of taurocholate. Colonies were enumerated after overnight growth, and data were compared to those for spores spread on BHIS(TA). Data are means from three independent experiments, and error bars represent 1 standard deviation from the mean.

Taurocholate Exposure Enhances Colony Formation by *C. Difficile* Spore In Vitro Inclusion of 0.1% taurocholate in BHIS agar plates enhanced the recovery of *C. difficile* spores approximately $10^5$-fold. To determine how long an exposure to taurocholate is required to increase colony formation, spores and vegetative bacteria were heated at 60° C. for 20 mM and washed three times with water to remove traces of nutrients that may affect germination. Spores were then returned to the anaerobic chamber and treated with 0.1% taurocholate in water (FIG. 2). At the indicated times, samples were removed, diluted in BHI medium, and plated on BHIS agar (without taurocholate). One sample was not incubated in vitro with taurocholate but was plated directly on BHIS(TA). This sample served as a reference for 100% recovery. As shown in FIG. 2, as little as 1 minute of exposure to taurocholate resulted in an increase in spore recovery from 0.0025% to about 1%. Further incubation did not significantly enhance colony formation by *C. difficile* spores. These results demonstrate that *C. difficile* spores respond very rapidly to taurocholate, suggesting that taurocholate may be a germinant.

Example 2

Figure 3:
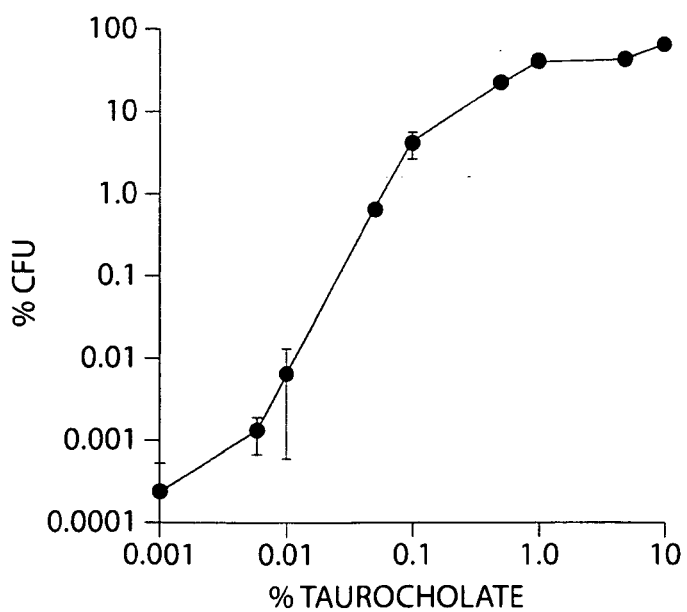
FIG. 3 is a graph depicting amount of taurocholate required for efficient recovery of C. difficile spores. C. difficile spores were incubated in water containing increasing concentrations of taurocholate, serially diluted, and plated on BHIS agar in the absence of taurocholate. Colonies were enumerated after overnight growth, and data were compared to those for spores spread on BHIS(TA). Data points are means from three independent experiments, and error bars represent 1 standard deviation from the mean.

Dependence of *C. Difficile* Spore Colony Formation on Taurocholate Concentration Because colony-forming ability in response to 0.1% taurocholate did not reach that of spores plated on BHIS(TA) directly, the in vitro recovery of spores in response to different concentrations of taurocholate was tested. Spores were prepared as described above, washed with water to remove traces of nutrients, incubated for 10 min with taurocholate at concentrations ranging from 0.001% to 10%, and plated on BHIS agar without taurocholate. Spore colony-forming ability was compared to that of spores plated directly on BHIS(TA). Incubation of spores with 0.001% taurocholate resulted in colony formation by approximately 0.0002% of the total number of spores (FIG. 3). This efficiency of colony formation was routinely observed in the absence of any taurocholate and can vary approximately 10-fold (FIG. 2). Increasing the concentration of taurocholate increased the plating efficiency of *C. difficile* spores (FIG. 3). Incubation for 10 min in 10% taurocholate resulted in a plating efficiency that was 60% of that seen with continuous exposure to 0.1% taurocholate (FIG. 3). This result suggests that continuous exposure to a low concentration of taurocholate significantly enhances colony formation even further or that the effect of taurocholate is enhanced when spores are in contact with a solid surface or both.

Example 3

*C. Difficile* Germination in Response to Primary Bile Salts

Figure 4A:
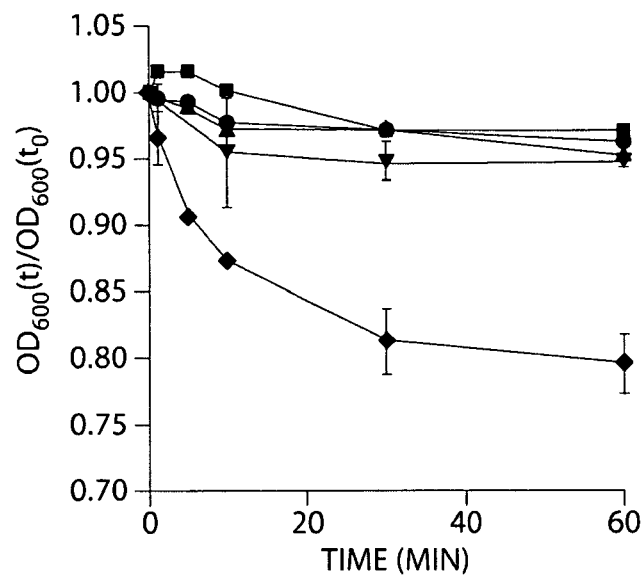
FIG. 4 is a series of graphs depicting effect of primary bile salts on the germination and growth of C. difficile. (A) C. difficile CD196 spores were purified and suspended in BHIS alone (●), in 1% taurocholate in buffer (▼), or in BHIS containing 1% taurocholate (♦), 1% glycocholate (▲), or 1% cholate (■). The ratios of the optical densities at various time points to the starting optical density are plotted against time. (B) C. difficile CD196 spores were purified and suspended in buffered glycine (1.3 mM) (▲), buffered 1% taurocholate (▼), or buffered glycine plus taurocholate (♦). Germination was measured as for panel A. (C)C. difficile UK14 spores were purified and suspended in buffered glycine (1.3 mM) (▲), buffered 1% taurocholate (▼), or buffered glycine plus taurocholate (♦). Germination was measured as for panel A. (D) Vegetative C. difficile (solid lines) and vegetative C. perfringens (dashed lines) were grown in BHIS alone (●), BHIS (TA) (♦), or BHIS plus 0.1% chenodeoxycholate (x). Error bars represent 1 standard deviation from the mean.

In *B. subtilis* and other species, the addition of a germinant to spores results in a change from phase bright (refractile) spores to phase dark spores due to the release of $Ca^{2+}$-DPA and rehydration of the spore. Moir et al. (1990) *Annu. Rev. Microbiol.* 44:531-553. This transition is the first stage of germination, can be measured as a decrease in the optical density of the culture, and can be used to define germinants. To see if taurocholate enhances colony formation by increasing the rate or extent of spore germination, *C. difficile* spores were incubated in phosphate buffer (pH 7.2) with 1% taurocholate or in buffer alone. One percent taurocholate was chosen because this concentration enabled colony formation by about 30% of the total number of spores during in vitro exposure (FIG. 3). At regular intervals, the $OD_{600}$ was measured and plotted against time. By this measure, taurocholate did not induce germination of *C. difficile* spores (FIG. 4A). To see if spores germinate in BHIS medium but become arrested before acquiring the ability to form colonies, spores were suspended in BHIS medium, and the optical density of the culture was monitored. No significant decrease in optical density was seen (FIG. 4A), indicating that spores do not germinate in BHIS alone. This result is in agreement with earlier observations that *C. difficile* spores do not efficiently form colonies in standard media without additional reagents. Wilson et al. (1982) *J. Clin. Microbiol.* 15:443-446. The addition of 1% taurocholate to BHIS resulted in a rapid decrease in the optical density to about 85% of the starting value, with a continued decrease to about 80% of the starting value (FIG. 4A). This is similar to what is seen for germination of *Clostridium botulinum* spores; the rate of germination appears to be higher in *C. difficile*. Broussolle et al. (2002) *Anaerobe* 8:89-100. These results suggest that taurocholate and an unknown component of BHIS medium are cogerminants of *C. difficile* spores; neither cogerminant activates germination by itself.

Example 4

*C. Difficile* Spore Germination and Colony Formation in Response to Primary Bile Salts Taurocholate is a primary bile salt produced by the liver and secreted to aid in digestion. To test the effect of other primary bile salts on colony formation, spores were plated on BHIS agar containing 0.1% cholate, glycocholate, chenodeoxycholate, ursodeoxycholate, or taurocholate. Interestingly, only cholate derivatives (cholate, glycocholate, and taurocholate) stimulated efficient colony formation by *C. difficile* spores (Table 1). Chenodeoxycholate and ursodeoxycholate, the 7β epimer of chenodeoxycholate, were not effective in this assay (Table 1). The primary bile salts cholate and glycocholate were then compared to taurocholate for germination-inducing ability. Incubation of *C. difficile* spores in BHIS with glycocholate or cholate did not result in any significant decrease in the optical density of the culture even when the assay was carried out to 6 h (FIG. 4A). Thus, glycocholate and cholate enhance colony formation by spores on plates but do not stimulate germination per se by the assay used.

TABLE 1

Cholate derivatives induce colony formation by *C. difficile* spores

| Cholate derivative added to BHIS[a] | CFU recovery (%)[b] | |
|---|---|---|
| | Mean | SD |
| TA | 100 | |
| GA | 86.3 | 17.2 |
| CA | 75.1 | 10.3 |
| CDCA | <0.0001[c] | |
| UA | <0.0001[c] | |

[a]Spores were serially diluted and spread on BHIS agar containing 0.1% taurocholate (TA), glycocholate (GA), cholate (CA), chenodeoxycholate (CDCA), or ursodeoxycholate (UA).
[b]Data are percentages relative to the value obtained with BHIS(TA) and are means of three independent experiments.
[c]CFU for CDCA and UA were below the limit of detection for this experiment.

Example 5

Glycine is a Cogerminant for *C. Difficile* Spores

Figure 4B:
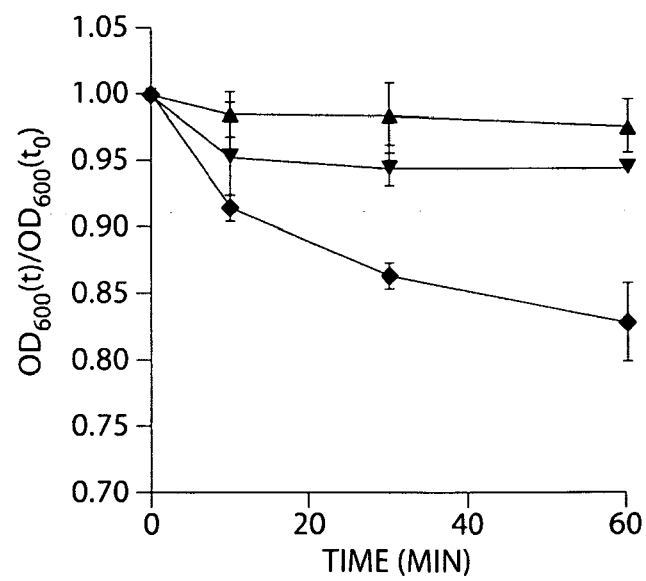

To identify the component of BHIS that induces germination with taurocholate, the medium was divided into BHI and yeast extract. In the presence of taurocholate, both BHI and yeast extract induced germination of *C. difficile* spores. Defined medium described by Karlsson and colleagues (Karlsson et al. (1999) *Microbiology* 145:1683-1693) was used to identify the specific compound or compounds that induce germination. When spores were suspended in complete defined medium with taurocholate, the optical density of the culture decreased to the same extent as in BHIS(TA). When this medium was divided into it constituents and sub-constituents, it was found that spores suspended in buffer containing glycine germinated in the presence of taurocholate but not in its absence (FIG. 4B). These results indicate that glycine and taurocholate are cogerminants.

Figure 4C:
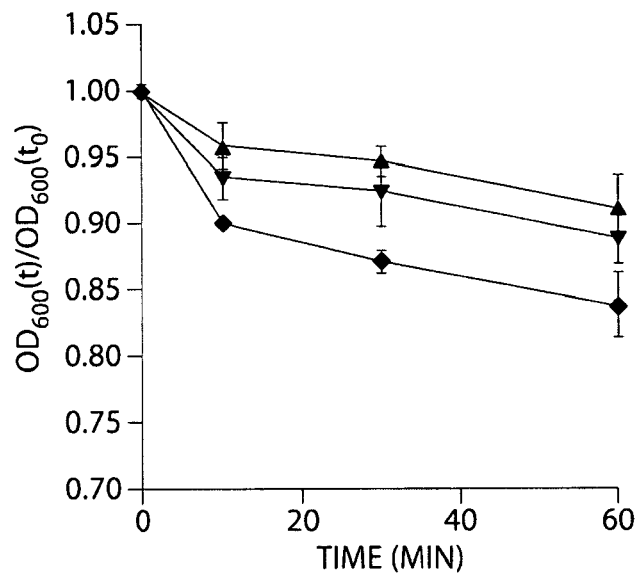

To test whether glycine and taurocholate act as cogerminants for another strain of *C. difficile*, another strain, UK14, isolated during an outbreak at Stoke-Mandeville Hospital in the United Kingdom, was studied. When *C. difficile* UK14 spores were suspended in buffer containing glycine or taurocholate alone, a small decrease in the optical density of the culture was observed (FIG. 4C). When both glycine and taurocholate were present, the efficiency of germination was enhanced (FIG. 4C). These results confirmed the results in *C. difficile* CD196 that taurocholate and glycine act as cogerminants for *C. difficile* spores.

Example 6

Effect of Primary Bile Salts on the Growth of *C. Difficile* Vegetative Cells

Figure 4D:
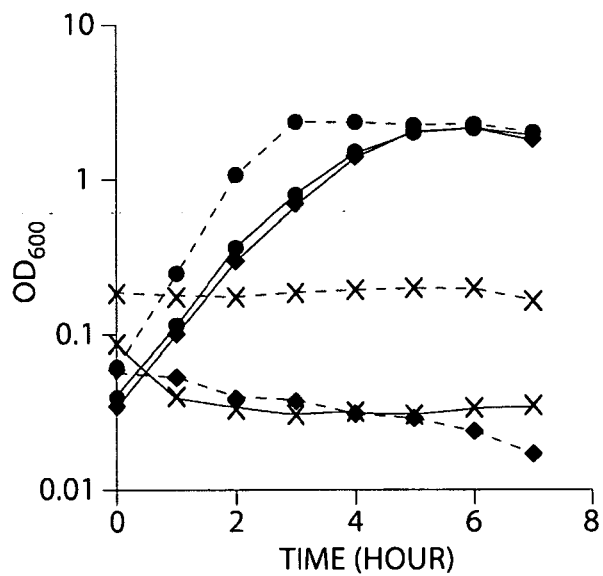

The ability of vegetative cells of *C. difficile* to grow in the presence of the primary bile salts was studied. As expected, *C. difficile* was able to grow in BHIS containing 0.1% taurocholate, glycocholate, or cholate to the same extent as in BHIS medium alone (FIG. 4D). *C. difficile* was unable to grow in the presence of chenodeoxycholate. Therefore, the absence of growth demonstrated by the data in Table 1 can be explained by growth inhibition by chenodeoxycholate. In contrast to *C. difficile*, *C. perfringens* SM101 was unable to grow in the presence of either 0.1% taurocholate or 0.1% chenodeoxycholate (FIG. 4D). Heredia et al. (1991) *FEMS Microbiol. Lett.* 84:15-22. *C. perfringens* SM101 was able to grow, however, to wild-type levels in the presence of glycocholate and cholate. These results suggest that *C. difficile* may have evolved a mechanism to resist the toxic effects of taurocholate in addition to sensing taurocholate as a germinant.

TABLE 2

Colony formation of *C. difficile* spores

| Treatment[a] | CFU recovery (%)[b] | |
|---|---|---|
| | Mean | SD |
| None | 100 | |
| TA | 1.27 | 0.38 |
| CDCA | 0.0012 | 0.001 |
| DCA | 1.48 | 0.27 |

[a]Spores were treated in vitro with 0.1% taurocholate (TA), chenodeoxycholate (CDCA), or deoxycholate (DCA), serially diluted, and spread on BHIS agar.
[b]Data are percentages relative to the value obtained with BHIS(TA) and are means of three independent experiments.

Chenodeoxycholate inhibited the growth of vegetative cells of *C. difficile* and *C. perfringens*. To test whether transient exposure to chenodeoxycholate induces colony formation by *C. difficile* spores, spores were suspended in water containing 0.1% chenodeoxycholate for 10 min, serially diluted in BHIS medium, and plated on BHIS agar in the absence of chenodeoxycholate. Exposure to chenodeoxycholate did not induce colony formation by *C. difficile* spores (Table 2). These results suggest that *C. difficile* spores only germinate in BHIS and form colonies in response to cholate derivatives (taurocholate, glycocholate, and cholate).

Example 7

Deoxycholate Induces Colony Formation but Prevents the Growth of *C. Difficile*

Figure 5A:
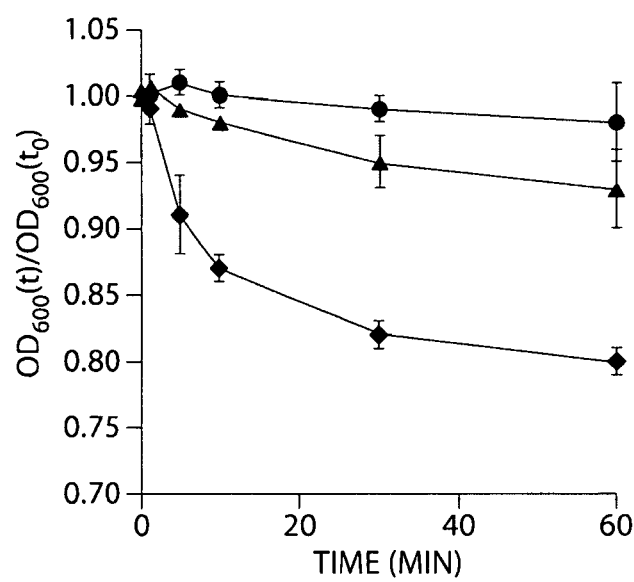
FIG. 5 is a pair of graphs depicting effect of deoxycholate on the germination and growth of C. difficile. (A) C. difficile spores were purified and suspended in BHIS alone (●) or in BHIS(TA) (♦) or BHIS+1% deoxycholate (▲). (B) Vegetative C. difficile (solid lines) and vegetative C. perfringens (dashed lines) were grown in BHIS alone (●) or BHIS plus 0.1% deoxycholate (▲). Error bars represent 1 standard deviation from the mean.

Deoxycholate was tested for its ability to induce the germination or recovery of *C. difficile* spores. Lithocholate could not be tested, as it is insoluble in water. When *C. difficile* spores were incubated in vitro with 0.1% deoxycholate, serially diluted, and plated on BHIS agar, colony-forming ability was indistinguishable from that of spores incubated with taurocholate (Table 2). These results suggest that deoxycholate, like other cholate derivatives, induces colony formation by *C. difficile* spores (Tables 1 and 2). Incubation of *C. difficile* spores in BHIS with 1% deoxycholate resulted in a small drop in $OD_{600}$ that after 60 min was not significantly more than the change in OD of spores in BHIS alone (FIG. 5A).

Figure 5B:
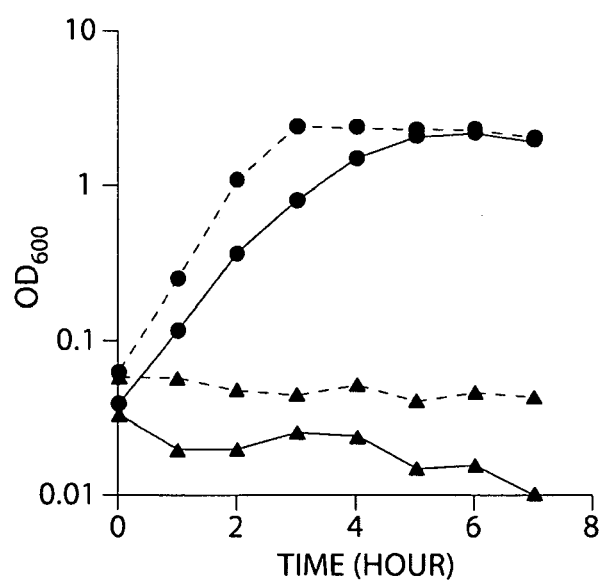

*C. difficile* does not grow in the presence of deoxycholate. Wilson (1983) *J. Clin. Microbiol.* 18:1017-1019. To quantify this effect, the growth of *C. difficile* and *C. perfringens* in BHIS containing deoxycholate was measured. Although *C. difficile* grew well in medium containing taurocholate, neither *C. difficile* nor *C. perfringens* grew in the presence of deoxycholate (FIG. 5B).

Example 8

Chenodeoxycholate Inhibits Colony Formation by *C. Difficile* Spores in Response to Taurocholate and Cholate

Figure 6A:
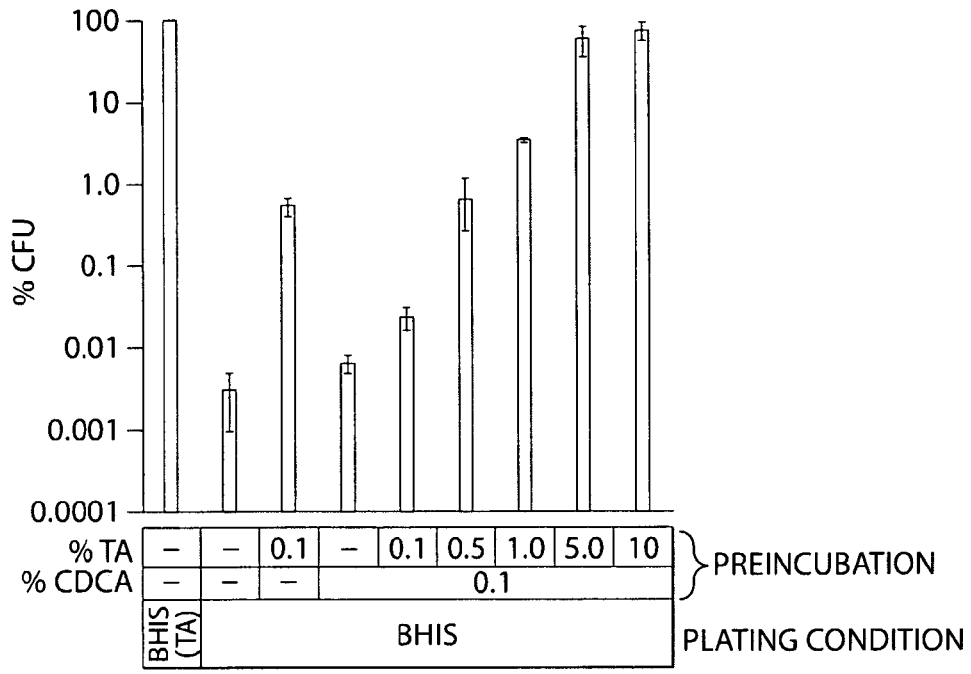
FIG. 6 is a pair of bar graphs depicting chenodeoxycholate-mediated inhibition of colony formation of C. difficile. (A) Colony formation in response to taurocholate (TA) with and without chenodeoxycholate (CDCA). (B) Colony formation in response to cholate (CA) with and without chenodeoxycholate (CDCA). Note the Y-axis in each graph is logarithmic.
Figure 6B:
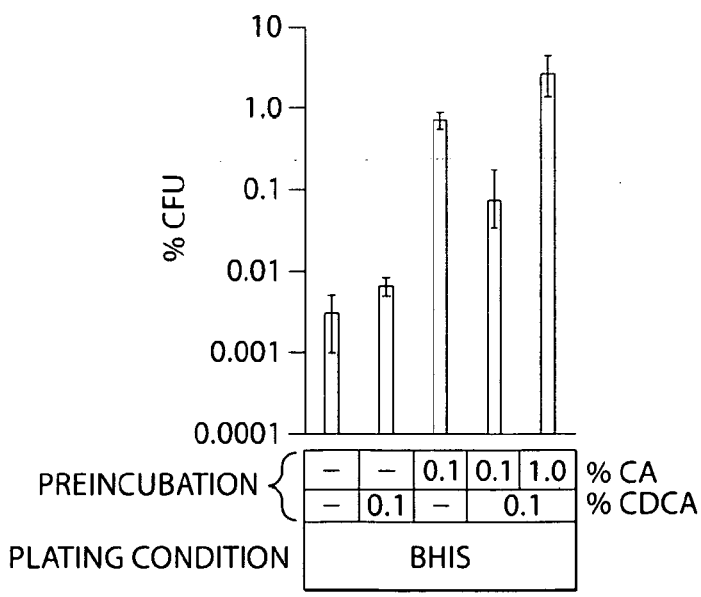

*C. difficile* spores were prepared and exposed to taurocholate (TA) or chenodeoxycholate (CDCA) or both in water for 10 minutes before serial dilution and plating on BHIS agar in the absence of taurocholate. Spores plated on BHIS(TA) served as a positive control for 100% colony formation (CFU). In a separate experiment *C. difficile* spores were prepared and exposed to cholate (CA) or chenodeoxycholate (CDCA) or both in water for 10 minutes before serial dilution and plating on BHIS agar in the absence of taurocholate. Results are shown in FIG. 6. As shown in FIG. 6A, chenodeoxycholate inhibited colony formation (germination) by spores treated with taurocholate. As shown in FIG. 6B, chenodeoxycholate inhibited colony formation (germination) by spores treated with cholate. These results indicate that chenodeoxycholate inhibits colony formation (germination) by *C. difficile* spores in response to taurocholate and cholate.

Example 9

Chenodeoxycholate is an Anti-Germinant for *C. Difficile* Spores

Figure 7:
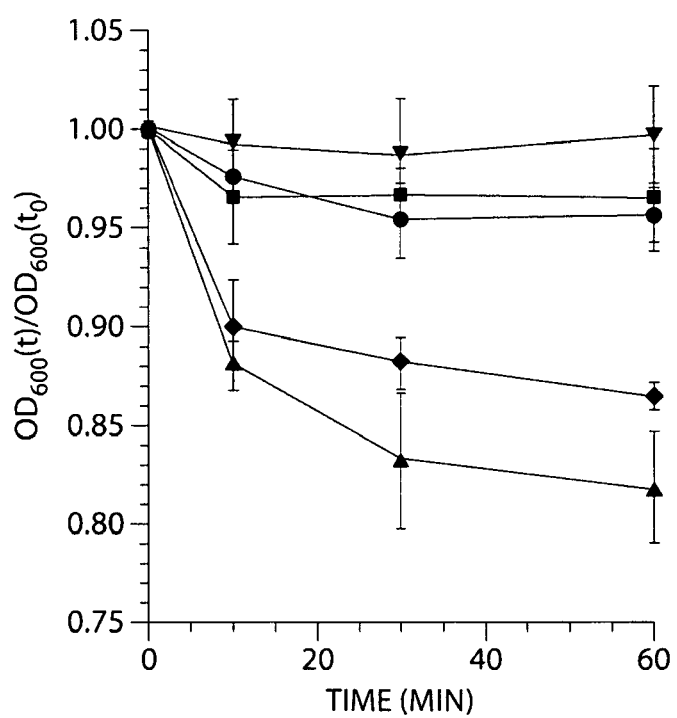
FIG. 7 is a graph depicting chenodeoxycholate-mediated inhibition of germination of C. difficile. C. difficile spores were suspended in BHIS alone (●), BHIS+0.1% CDCA (▼), BHIS+0.1% TA (♦), BHIS+0.1% TA/0.1% CDCA (■) or BHIS+1.0% TA/0.1% CDCA (▲). The ratio of the $OD_{600}$ at the indicated time points to the $OD_{600}$ at $T_0$ is plotted vs. time. Data points are the averages of three independent experiments and error bars represent one standard deviation from the mean.

*C. difficile* spores were suspended in BHIS alone (●), BHIS+0.1% CDCA (▼), BHIS+0.1% TA (♦), BHIS+0.1% TA/0.1% CDCA (■) or BHIS+1.0% TA/0.1% CDCA (▲). Optical density was measured as a function of time, where a decrease in optical density indicates germination. Results are shown in FIG. 7. As shown in FIG. 7, the ratio of the $OD_{600}$ at various time points to the $OD_{600}$ at $T_0$ decreased significantly for spores treated with 0.1% TA or with 1.0% TA/0.1% CDCA, indicating germination. In contrast, the ratio of the $OD_{600}$ at the various time points to the $OD_{600}$ at $T_0$ remained nearly unchanged for spores treated with 0.1% CDCA or 0.1% TA/0.1% CDCA, similar to spores suspended in BHIS alone. These results indicate that chenodeoxycholate is an anti-germinant for *C. difficile* spores and that it can inhibit germination by competing with taurocholate.

Example 10

Representative Conversion of a Bile Salt Carboxylic Acid to an Amino Derivative

Representative synthetic conversions of a bile salt carboxylic acid to an amino derivative are shown in Scheme 1. The acid, such as but not limited to, chenodeoxycholate (I), is converted to the methyl ester with dimethyl sulfate ($Me_2SO_4$) and sodium bicarbonate ($NaHCO_3$) in refluxing acetone. Silyl protection of the secondary alcohols is accomplished with numerous such reagents, including (2-chloroethyl)trimethylsilane ($Me_3SiCH_2CH_2Cl$), in the presence of sodium hydride (NaH) and dimethylformamide (DMF), which results in ester (II). Reduction of the methyl ester to the primary alcohol is accomplished with lithium aluminum hydride ($LiAlH_4$) in tetrahydrofuran (THF). Bromination of the resulting alcohol is effected with phosphorus tribromide ($PBr_3$) in dichloromethane ($CH_2Cl_2$), which yields alkyl bromide (III). The SN2 displacement of alkyl bromide (III) may be carried out with primary or secondary amines, such as but not limited to, sarcosine methyl ester (the N-methyl-glycine methyl ester) in DMF with NaH. Saponification of the resulting methyl ester is conducted with sodium hydroxide (NaOH) in methanol (MeOH), and cleavage of the silyl protecting groups is achieved with tetrabutylammonium fluoride in refluxing THF, which yields dihydroxy carboxylic acid (IV).

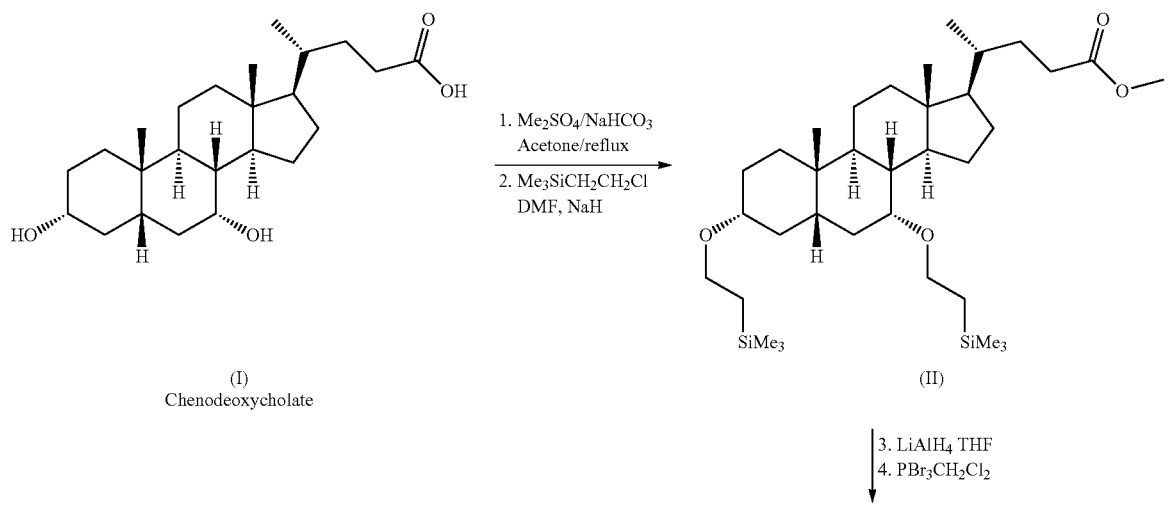

Scheme 1

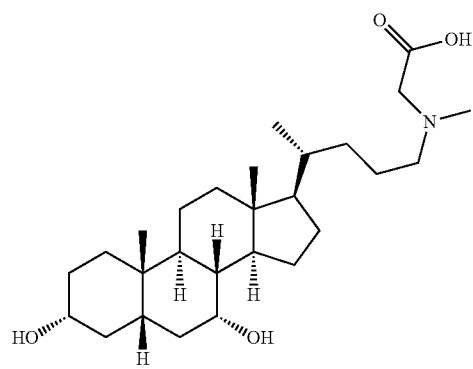
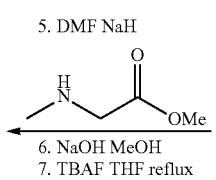
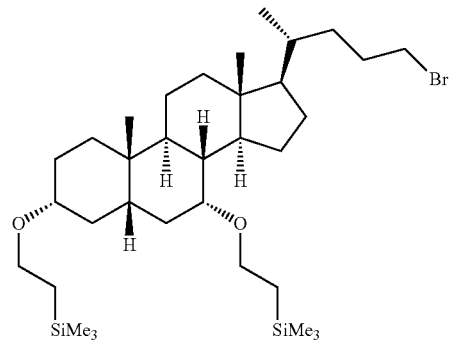

(IV)
Amino derivative of Chenodeoxycholate (III)

Example 11

Representative Conversion of a Bile Salt Carboxylic Acid to an Amide Derivative Representative synthetic conversions of a bile salt carboxylic acid, including chenodeoxycholate, to an amide derivative are shown in Scheme 2.

Chenodeoxycholate (I) and primary or secondary amines, including sarcosine methyl ester are converted to amides with standard peptide coupling reagents such as O-Benzotriazole-N,N,N',N'-tetramethyl-uronium-hexafluoro-phosphate (HBTU) in DMF and triethylamine ($Et_3N$). Saponification of the resulting methyl ester to carboxylic acid (V) is conducted with sodium hydroxide in methanol.

Scheme 2

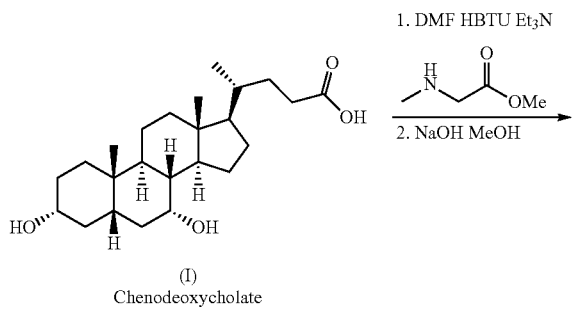
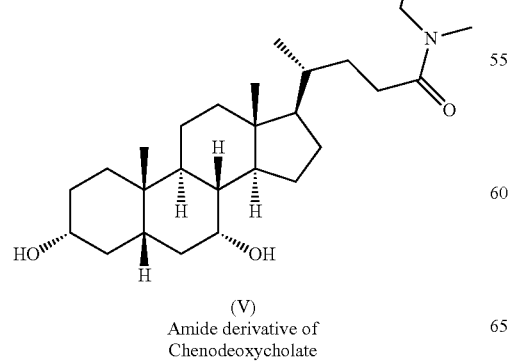

(V)
Amide derivative of Chenodeoxycholate

Example 12

Representative Conversion of a Bile Salt Carboxylic Acid to an N-Alkyl Derivative N-alkylation of bile salt derivatives has been shown to inhibit deconjugation, or cleavage of the amide linkage to a carboxylic acid, in vivo. In rats, the deconjugation of N-ethyl-tauroursodeoxycholate (3.4+/−2.1% after 72 hours) was inhibited relative to that of tauroursodeoxycholate (100% after 24 hours). Angelico et al. (1995) *Hepatology* 22:887-95. In humans, cholylsarcosine—the N-methyl derivative of glycocholate—was shown to be resistant to deconjugation as it was not biotransformed by hepatic or bacterial enzymes. Schmassmann et al. (1993) *Gastroenterology* 104:1171-81.

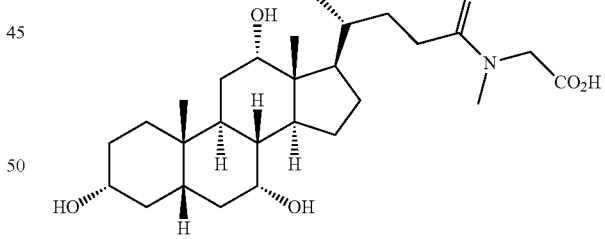

Cholylsarcosine

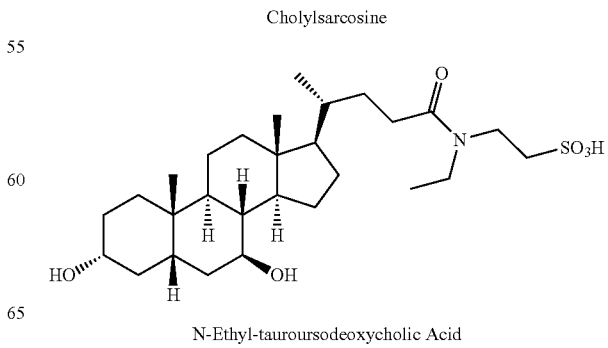

N-Ethyl-tauroursodeoxycholic Acid

Example 13

In Vivo Administration of Chenodeoxycholate Reduces Incidence of *C. Difficile* Colitis Hamsters, rats, mice, rabbits, dogs, or pigs are divided into two groups, a treatment group and a control group. Animals in both groups are treated with high-dose clindamycin or cephalosporin for 5 to 14 days. Animals in the treatment group also receive chenodeoxycholate 10 to 30 mg/kg body weight/day by gavage during the entire period they receive antibiotic. All animals are monitored for the development of *C. difficile* colitis by monitoring for the development of diarrhea containing *C. difficile* toxin. A reduced incidence of *C. difficile* colitis in the treatment group compared to the control group indicates that chenodeoxycholate reduces incidence of *C. difficile* colitis in animals at risk of developing *C. difficile* colitis.

Example 14

In Vivo Administration of *C. Scindens* Reduces Incidence of *C. Difficile* Colitis Hamsters, rats, mice, rabbits, dogs, or pigs are divided into two groups, a treatment group and a control group. Animals in both groups are treated with high-dose clindamycin or cephalosporin for 2 to 14 days. Animals in the treatment group also receive microencapsulated *C. scindens* 10 to 30 mg/kg body weight/day by gavage beginning within 24 h after conclusion of the period they receive antibiotic. All animals are monitored for the development of *C. difficile* colitis by monitoring for the development of diarrhea containing *C. difficile* toxin. A reduced incidence of *C. difficile* colitis in the treatment group compared to the control group indicates that *C. scindens* reduces incidence of *C. difficile* colitis in animals at risk of developing *C. difficile* colitis.

Example 15

In Vitro Inhibition of *C. Difficile* Spore Germination by Derivatives of Chenodeoxycholate In vitro experiments similar to those described in Example 3, based on optical density measurements, were performed with varying concentrations of chenodeoxycholate, ursodeoxycholate, and derivatives thereof, listed below, to determine activity and binding constants for inhibitors of *C. difficile* spore germination.

BHIS medium containing different concentrations of taurocholate (2 mM, 5 mM, 10 mM, 20 mM or 50 mM) was prepared and inhibitor was added. Solutions without inhibitor were used as a control to determine the $K_m$ for taurocholate in the absence of inhibitor. Spores were added and germination was measured as a change in $OD_{600}$ vs. time. The data were plotted and the maximum rate of germination under each condition was determined using the slope of the linear range of the plot. The inverse of the maximum rate of germination vs. the inverse of the taurocholate concentration was plotted (Lineweaver-Burk plot). From this graph, the $K_m$ (the concentration at which half-maximal germination rate was observed) for taurocholate was extrapolated and used to determine the binding constant for the inhibitor ($K_i$—the affinity of the compound for the spore; the lower the number, the tighter the interaction) using the equation:

$$K_i = [I]/((K_{obs}/K_m) - 1)$$

where [I] is the concentration of inhibitor used, $K_{obs}$ is the observed binding constant for taurocholate in the presence of inhibitor, and $K_m$ is the binding constant for taurocholate in the absence of inhibitor. Results are shown in Table 3.

TABLE 3

Selected inhibitors of *C. difficile* spore germination

| Compound | Source | Inhibits Germination? | $K_i$ (mM) |
|---|---|---|---|
| Chenodeoxycholate | | Yes | 0.3 |
| Ursodeoxycholate | Alfa #B20490-03 | Yes | 0.645 |
| 6-ketolithocholate | Steraloids #C1560-000 | Yes | 0.2 |
| 5β-cholanic acid 3α,7α diol diacetate methyl ester | Steraloids #C0964-000 | Yes | 0.04 |
| 5β-cholanic acid 3α,6β diol methyl ester | Steraloids #C0915-000 | Yes | 0.048 |
| 5β-cholanic acid 3α,7α diol methyl ester | Steraloids #C0975-000 | Yes | 0.022 |
| 5β-cholanic acid 3α,7α diol 3-acetate methyl ester | Steraloids #C0950-000 | Yes | 0.04 |
| 5β-cholanic acid 3α-ol-acetate | Steraloids #C1421-000 | No | — |
| Taurochenodeoxycholate | Steraloids #C0992-000 | No | — |

It was observed that 37DAME (5β-cholanic acid-3α,7α-diol diacetate methyl ester (5β-cholan-24-oic acid-3α,7α-diol methyl ester 3,7-diacetate) (CAS No. 2616-71-9; Steraloids catalog no. C0964-000)) inhibits *C. difficile* spore germination with a $K_i$ of 0.04 mM, i.e., about one log lower than that of chenodeoxycholate. That is, 37DAME was observed to be approximately ten times more potent an inhibitor of *C. difficile* spore germination than chenodeoxycholate. In addition, it was found that 37DAME has an affinity for *C. difficile* spores that is approximately 7-8 times greater than that of chenodeoxycholate.

In this particular experiment, neither 5β-cholanic acid 3α-ol-acetate nor taurochenodeoxycholate was observed to inhibit *C. difficile* spore germination.

Example 16

Exemplary Routes of Synthesis for Certain Bile Salt Derivatives Starting from 5β-cholanic acid-3α,7α-diol methyl ester A number of bile salt derivatives of interest are prepared using standard methods, starting with 5β-cholanic acid-3α,7α-diol methyl ester (e.g., Steraloids Catalog No. C0975-000).

Scheme 3
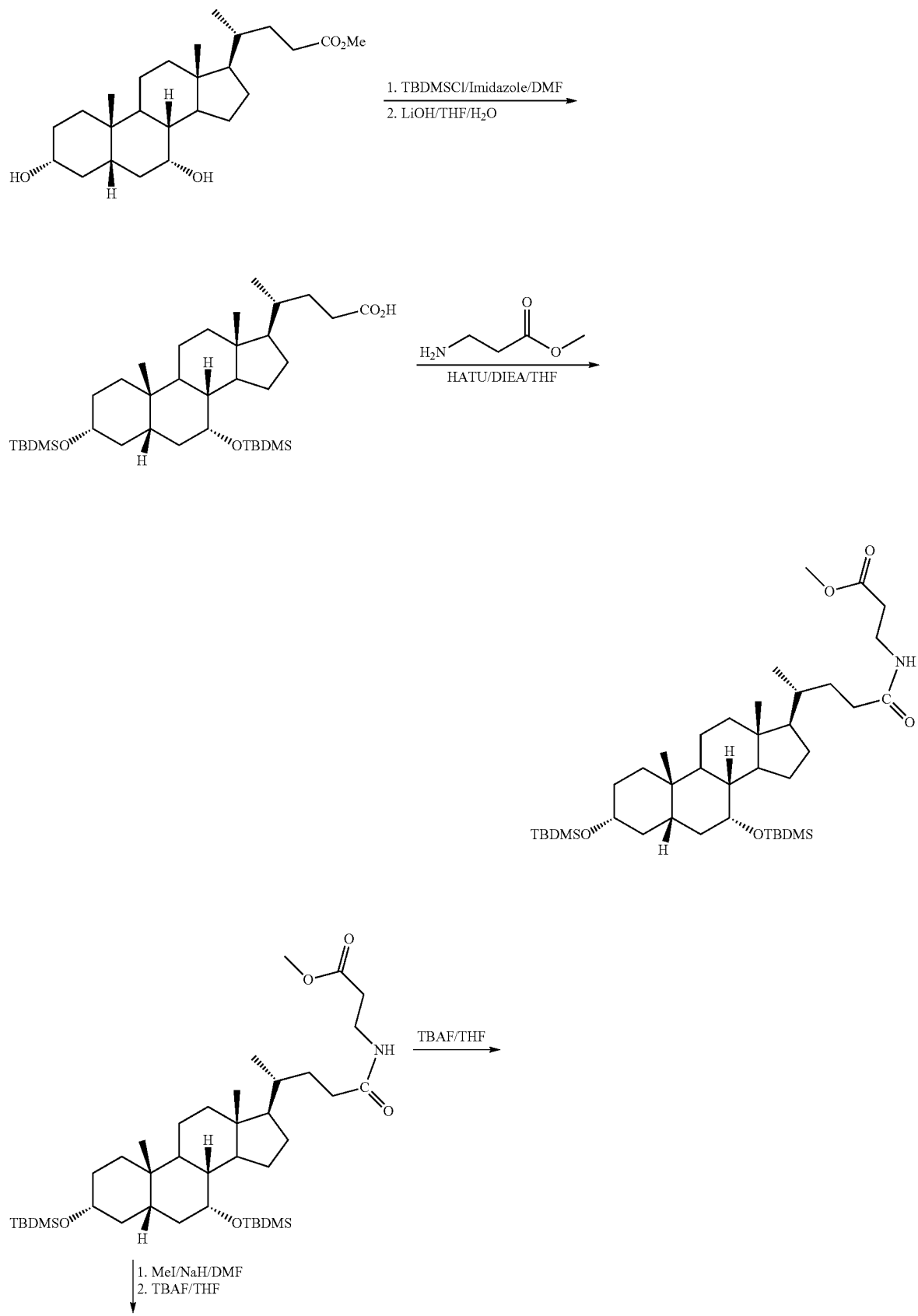

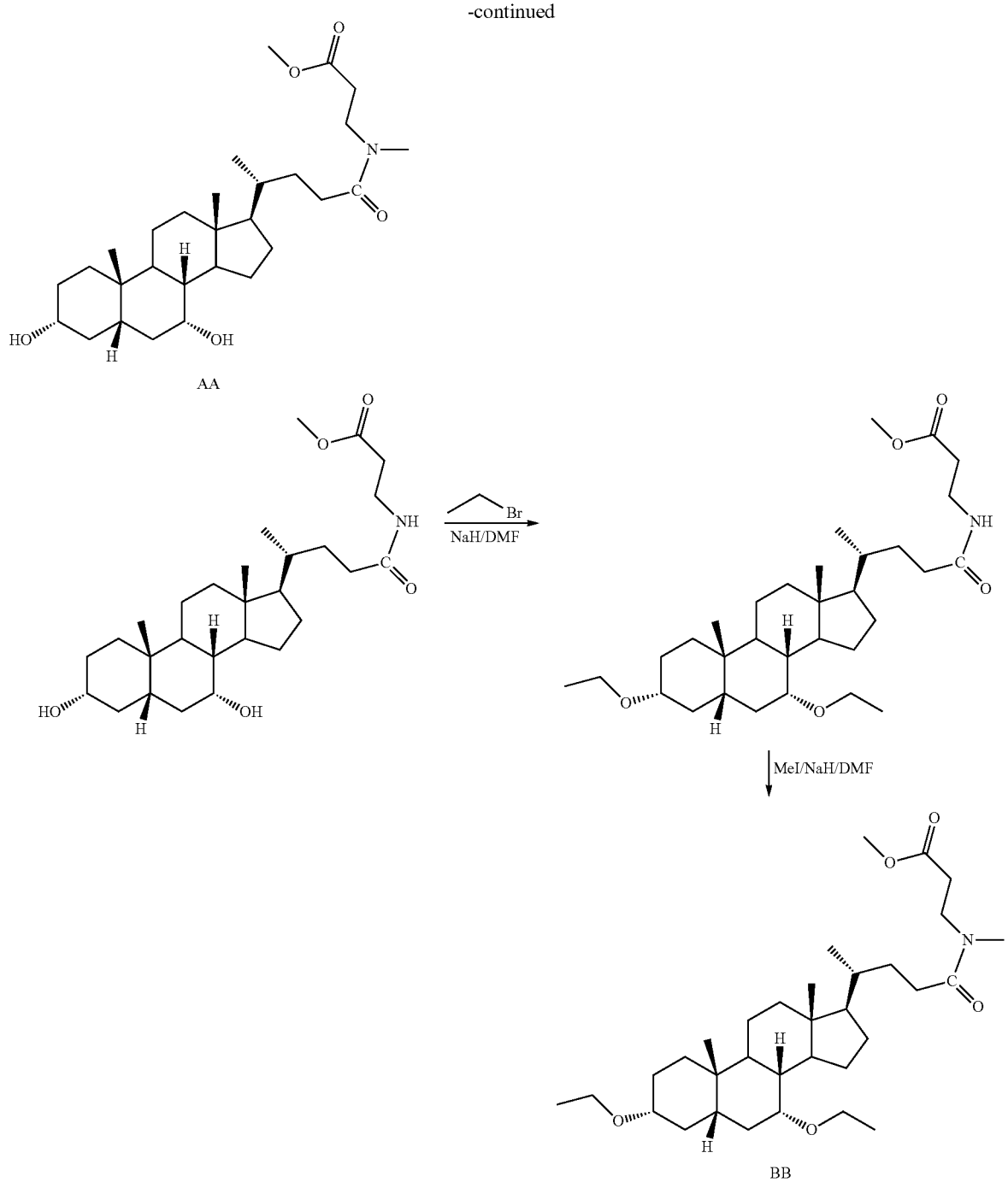

Representative synthetic conversions of bile salt esters to amide derivatives are shown in Scheme 3. For example, a diol, such as but not limited to methylchenodeoxycholate, can be converted to the corresponding disilylether upon exposure to t-butyldimethylsilyl chloride (TBDMS) and imidazole in dimethylformamide (DMF). Subsequent hydrolysis of the methyl ester with lithium hydroxide (LiOH) in tetrahydrofuran (THF) and water yields the corresponding carboxylic acid, which can be converted to the corresponding amide with a primary or secondary amine, such as methyl 3-aminopropanoate, in the presence of a peptide coupling reagent such as 2-(1H-7-azabenzotriazol-1-yl)-1,1,3,3-tetramethyl uronium hexafluorophosphate (HATU) and a tertiary amine, such as diisopropylethyl amine (DIEA), in THF. Cleavage of the silyl ethers can be accomplished with tetrabutylammonium fluoride (TBAF) in THF. Alkylation of the resulting diol functionalities can be accomplished with an alkyl halide, such as ethyl bromide, in the presence of sodium hydride (NaH) in DMF. Alkylation of the amide nitrogen can be accomplished with methyl iodide (MeI) in the presence of sodium hydride (NaH) in DMF, yielding amide BB.

Alternatively, alkylation of the amide nitrogen can be accomplished prior to cleavage of the TBDMS silyl ethers, as shown, yielding amide AA.

Example 17
Exemplary Routes of Synthesis for Certain Bile Salt Sulfonate Derivatives Starting from 5β-cholanic acid-3α,7α-diol methyl ester
A number of bile salt sulfonate derivatives of interest are prepared using standard methods, starting with 5β-cholanic acid-3α,7α-diol methyl ester (e.g., Steraloids Catalog No. C0975-000).
Scheme 4
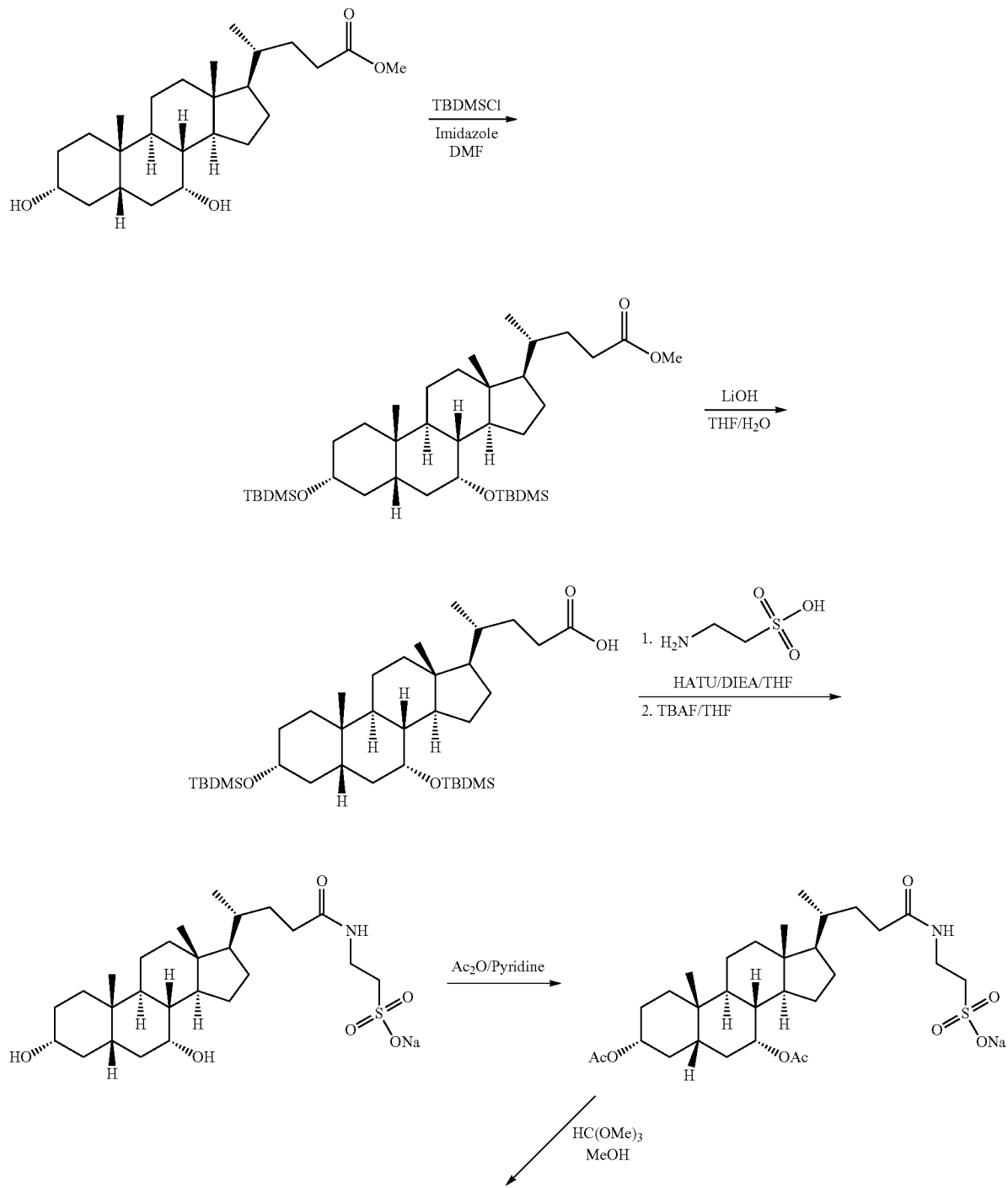

-continued

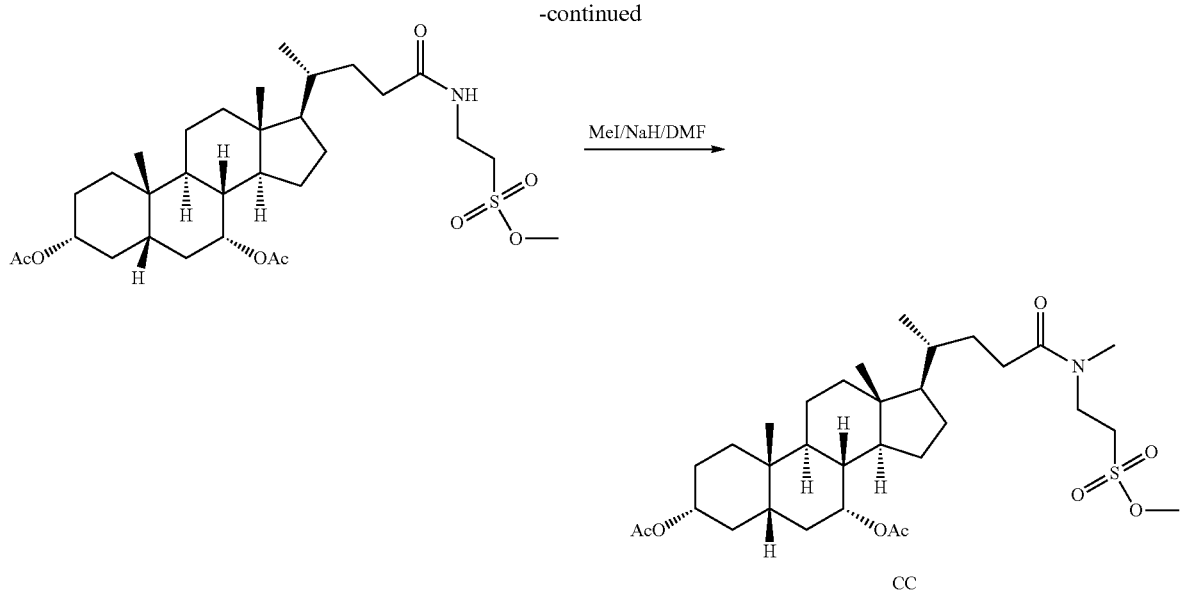

Representative synthetic conversions of bile salt esters to taurine-based amide derivatives are shown in Scheme 4. For example, a diol, such as but not limited to methylchenodeoxycholate, can be converted as the corresponding disilylether upon exposure to TBDMS and imidazole in DMF. Subsequent hydrolysis of the methyl ester with LiOH in THF and water yields the corresponding carboxylic acid, which can be converted to the corresponding amide with a primary or secondary amine, such as taurine (2-aminoethanesulfonic acid), in the presence of a peptide coupling reagent such as HATU and a tertiary amine, such as DIEA, in a solvent such as THF. Cleavage of the silyl ethers can be accomplished with TBAF in THF. Alkylation of the sulfonic acid functionality can be accomplished with trimethylorthoformate (HC(OMe)$_3$) in MeOH. Subsequent alkylation of the amide nitrogen can be accomplished with MeI in the presence of NaH in DMF, yielding the taurine-based amide derivative CC.

Example 18

Exemplary Routes of Synthesis for Certain Bile Salt Sulfonate Derivatives Starting from 5β-cholanic acid-3α,7α-diol n-(2-sulphoethyl)-amide sodium salt A number of additional bile salt sulfonate derivatives of interest are prepared using standard methods, starting with 5β-cholanic acid-3α,7α-diol n-(2-sulphoethyl)-amide sodium salt (e.g., Steraloids catalog no. C0992-000).

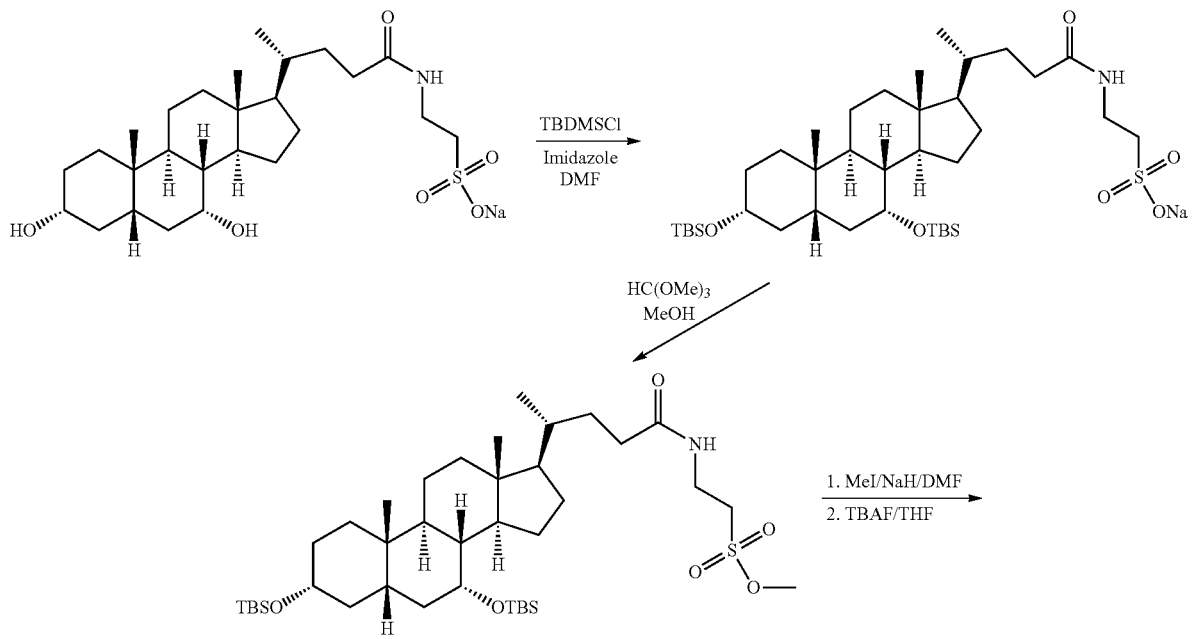

-continued

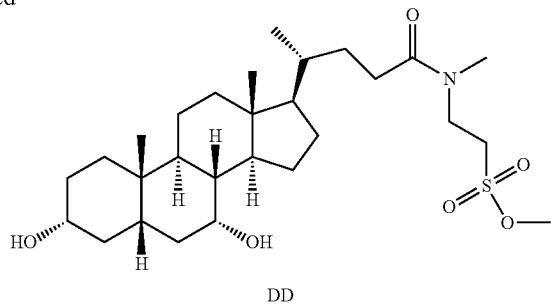

DD

Representative synthetic conversions of taurine-based amide derivatives are shown in Scheme 5. For example, the diol functionalities of a taurine-based amide derivative can be converted as the corresponding disilylether upon exposure to TBDMS and imidazole in DMF. Alkylation of the sulfonic acid functionality can be accomplished with trimethylorthoformate in MeOH. Subsequent alkylation of the amide nitrogen can be accomplished with MeI in the presence of NaH in DMF. Cleavage of the silyl ethers can be accomplished with TBAF in THF, yielding the taurine-based amide derivative DD.

Example 19

Exemplary Routes of Synthesis for Epimerization at Position 7

Various epimers are believed to be useful in the invention, including, for example, chenodeoxycholate and its 7β-epimer ursodeoxycholate. Epimers can be prepared following standard chemical methods, for example as follows:

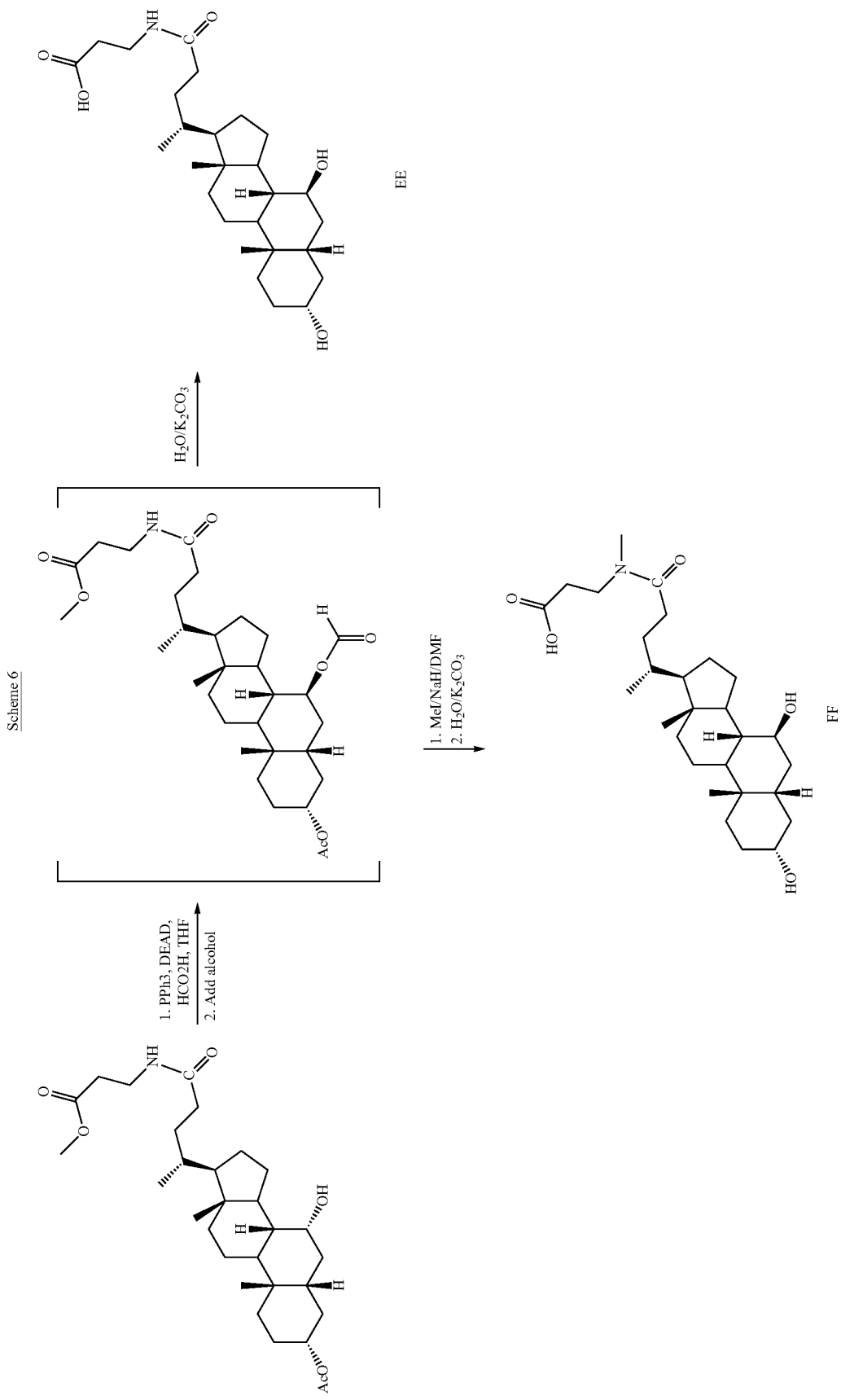

Epimerization of the bile salt derivatives can be accomplished under Mitsunobu conditions, as depicted in Scheme 6. To a THF solution of triphenylphosphine ($PPh_3$), diethyl azodicarboxylate (DEAD), and formic acid ($HCO_2H$) is added an alcohol, such as that shown in Scheme 6, to yield the corresponding formate ester. The formate ester may be hydrolyzed with aqueous potassium carbonate ($K_2CO_3$) to yield an alcohol EE of the opposite configuration relative to the starting alcohol. Alternatively, the amide nitrogen can first be alkylated with MeI in the presence of NaH in DMF, prior to hydrolysis of the formate ester, to yield alcohol FF.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of treating *Clostridium difficile*-associated disease in a mammalian subject, comprising administering to a mammalian subject having *C. difficile*-associated disease an effective amount of a compound of Formula I

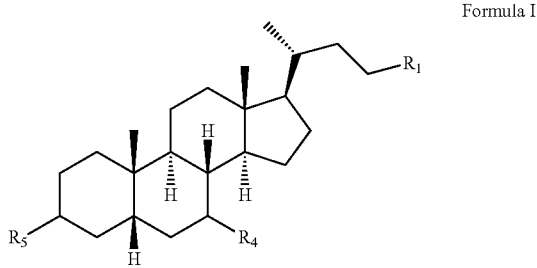

Formula I or a pharmaceutically acceptable salt thereof, wherein:
the compound is an inhibitor of *C. difficile* spore germination;
$R_1$ is selected from the group consisting of —$CO_2H$ and —$CO_2(R_2)$;
each $R_2$ is independently a straight or branched chain C1-C10 alkyl; and
each of $R_4$ and $R_5$ is independently selected from the group consisting of —OH and —OC(=O)(C1-C10 alkyl), to inhibit growth of *C. difficile* in the subject, thereby treating the *C. difficile*-associated disease, wherein the *C. difficile*-associated disease is selected from the group consisting of *C. difficile* colitis and pseudomembranous colitis.

2. The method of claim 1, wherein the compound of Formula I is chenodeoxycholate or a pharmaceutically acceptable salt thereof.

3. The method of claim 1, wherein the compound of Formula I is ursodeoxycholate or a pharmaceutically acceptable salt thereof.

4. The method of claim 1, wherein the mammalian subject is a human.

5. The method of claim 1, wherein:
$R_1$ is —$CO_2(R_2)$;
$R_2$ is methyl; and
both $R_4$ and $R_5$ are —OH.

6. The method of claim 1, wherein:
$R_1$ is —$CO_2(R_2)$;
$R_2$ is methyl;
$R_4$ is —OH; and
$R_5$ is —OC(=O)(C1-C10 alkyl).

7. The method of claim 1, wherein:
$R_1$ is —$CO_2(R_2)$;
$R_2$ is methyl;
$R_4$ is —OH; and
$R_5$ is —OC(=O)($CH_3$).

8. The method of claim 1, wherein:
$R_1$ is —$CO_2(R_2)$;
$R_2$ is methyl;
both $R_4$ and $R_5$ are —OC(=O)(C1-C10 alkyl).

9. The method of claim 1, wherein:
$R_1$ is —$CO_2(R_2)$;
$R_2$ is methyl;
both $R_4$ and $R_5$ are —OC(=O)($CH_3$).

10. A method of reducing risk of developing *Clostridium difficile*-associated disease in a mammalian subject receiving antibiotic therapy, comprising administering to a mammalian subject receiving antibiotic therapy and at risk of developing *C. difficile*-associated disease an effective amount of a compound of Formula I

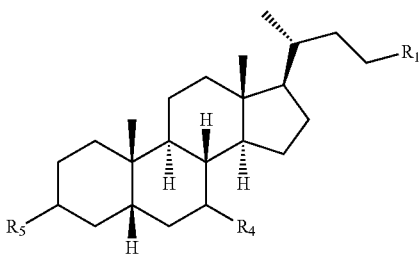

Formula I or a pharmaceutically acceptable salt thereof, wherein:
the compound is an inhibitor of *C. difficile* spore germination;
$R_1$ is selected from the group consisting of —$CO_2H$ and —$CO_2(R_2)$;
each $R_2$ is independently a straight or branched chain C1-C10 alkyl; and
each of $R_4$ and $R_5$ is independently selected from the group consisting of —OH and —OC(=O)(C1-C10 alkyl), to inhibit germination of *C. difficile* spores in the subject, thereby reducing the risk of developing *Clostridium difficile*-associated disease in the subject, wherein the *C. difficile*-associated disease is selected from the group consisting of *C. difficile* colitis and pseudomembranous colitis.

11. The method of claim 10, wherein:
$R_1$ is —$CO_2(R_2)$;
$R_2$ is methyl; and
both $R_4$ and $R_5$ are —OH.

12. The method of claim 10, wherein:
$R_1$ is —$CO_2(R_2)$;
$R_2$ is methyl;
$R_4$ is —OH; and
$R_5$ is —OC(=O)(C1-C10 alkyl).

13. The method of claim 10, wherein:
$R_1$ is —$CO_2(R_2)$;
$R_2$ is methyl;
$R_4$ is —OH; and
$R_5$ is —OC(=O)($CH_3$).

14. The method of claim 10 wherein:
$R_1$ is —$CO_2(R_2)$;
$R_2$ is methyl;
both $R_4$ and $R_5$ are —OC(=O)(C1-C10 alkyl).

15. The method of claim 10, wherein:
R$_1$ is —CO$_2$(R$_2$);
R$_2$ is methyl;
both R$_4$ and R$_5$ are —OC(=O)(CH$_3$).

16. The method of claim 10, wherein the mammalian subject is a human.

* * * * *